(12) United States Patent
Sundermann et al.

(10) Patent No.: US 7,211,694 B2
(45) Date of Patent: May 1, 2007

(54) SUBSTITUTED 4-AMINOCYCLOHEXANOLS

(75) Inventors: Bernd Sundermann, Aachen (DE); Hagen-Heinrich Hennies, Simmerath (DE); Werner Englberger, Stolberg (DE); Babette-Yvonne Koegel, Langerwehe-Hamich (DE)

(73) Assignee: Gruenenthal GmbH, Aachen (DE)

( * ) Notice: Subject to any disclaimer, the term of this patent is extended or adjusted under 35 U.S.C. 154(b) by 299 days.

(21) Appl. No.: 10/947,551

(22) Filed: Sep. 23, 2004

(65) Prior Publication Data

US 2005/0187220 A1 Aug. 25, 2005

Related U.S. Application Data

(63) Continuation of application No. PCT/EP03/02812, filed on Mar. 18, 2003.

(30) Foreign Application Priority Data

Mar. 23, 2002 (DE) ................. 102 13 051

(51) Int. Cl.
| | |
|---|---|
| C07C 211/38 | (2006.01) |
| C07D 277/62 | (2006.01) |
| C07D 209/04 | (2006.01) |
| C07D 333/56 | (2006.01) |
| C07D 333/72 | (2006.01) |
| C07D 317/72 | (2006.01) |
| C07D 307/94 | (2006.01) |

(52) U.S. Cl. ............... 564/307; 548/179; 548/469; 549/58; 549/341; 549/469; 514/367; 514/415; 514/443; 514/462; 514/469; 514/647

(58) Field of Classification Search .............. None
See application file for complete search history.

(56) References Cited

U.S. PATENT DOCUMENTS

| 4,366,172 A | 12/1982 | Lednicer |
| 4,446,065 A | 5/1984 | Lin et al. |

FOREIGN PATENT DOCUMENTS

| WO | WO 96/14307 | 5/1996 |
| WO | WO 02/30891 A1 | 4/2002 |

OTHER PUBLICATIONS

Abdulla and Smith, J. Neurosci. 18, 1998, p. 9685-9694.
Ardati et al., Mol. Pharmacol., 51, 1997, p. 816-824.
Bertorelli et al., Trends in Pharmacological Sciences, 21, 2000, p. 233-234.
Calo et al., Br. J. Pharmacol., 129, 2000, 1261-1283.
Camplon and Kadowitz, Biochem. Biophys. Res. Comm., 234, 1997, p. 309-312.
Conner et al., Br. J. Pharmacol. 118, 1996, p. 205-207.
Darland et al., Trends in Neurosciences, 21, 1998, p. 215-221.
Faber et al., Br. J. Pharmacol., 119, 1996, p. 189-190.
Gumusel et al., Life Sci., 60, 1997, p. 141-145.
Gutiérrez et al., Abstract 536.18, Society for Neuroscience, vol. 24, 28th Ann. Meeting, Los Angeles, Nov. 7-12, 1998.
Hara et al., Br. J. Pharmacol. 121, 1997, p. 401-408.
Jenck et al., Proc. Natl. Acad. Sci. USA 94, 1997, 14854-14858.
Kalir et al., Israel Journal of Chemistry, 13, 1975, p. 125-136.
Kapusta et al., Life Sciences, 60, 1997, PL 15-21.
King et al., Neurosci. Lett., 223, 1997, 113-116.
Knoflach et al., J. Neuroscience 16, 1996, p. 6657-6664.
Manabe et al., Nature, 394, 1997, p. 577-581.
Matthes et al., Mol. Pharmacol. 50, 1996, p. 447-450.
Meunier et al., Nature 377, 1995, p. 532-535.
Mogil et al., Neurosci. Letters 214, 1996, p. 131-134.
Mogil et al., Neuroscience 75, 1996, p. 333-337.
Mollereau et al., FEBS Letters, 341, 1994, p. 33-38.
Nishi et al., EMBO J., 16, 1997, p. 1858 1864.
Pomonis et al., NeuroReport, 8, 1996, p. 369-371.
Reinscheid et al., Science 270, 1995, p. 792-794.
Sandin et al., Eur. J. Neurosci., 9, 1997, p. 194-197.
Shu et al., Neuropeptides, 32, 1998, 567-571.
Vaughan et al., Br. J. Pharmacol. 117, 1996, p. 1609-1611.
Vignon et al., European Journal of Pharmacology, 81, 1982, p. 531-542.
Xu et al., NeuroReport, 7, 1996, 2092-2094.
Yamamoto and Nozaki-Taguchi, Anesthesiology, 87, 1997.
Yamamoto et al., Neuroscience, 81, 1997, p. 249-254.
International Search Report, 2003 for PCT EP/03/02812.

*Primary Examiner*—Brian Davis
(74) *Attorney, Agent, or Firm*—Crowell & Moring LLP

(57) ABSTRACT

Substituted 4-aminocyclohexanols, processes for their preparation, pharmaceutical compositions comprising these compounds and to the use of substituted 4-aminocyclohexanols in the preparation of pharmaceutical compositions for the treatment of various indications, especially pain as well as the treatment of these indications.

31 Claims, No Drawings

US 7,211,694 B2

SUBSTITUTED 4-AMINOCYCLOHEXANOLS

CROSS REFERENCE TO RELATED APPLICATIONS

This application is a continuation of international patent application no. PCT/EP03/02812, filed Mar. 18, 2003, designating the United States of America, and published in German as WO 03/080557, the entire disclosure of which is incorporated herein by reference. Priority is claimed based on German patent application no. 102 13 051.5, filed Mar. 23, 2002.

FIELD OF THE INVENTION

The present invention relates to substituted 4-aminocyclohexanols, to processes for their preparation, to pharmaceutical compositions comprising these compounds and to the use of substituted 4-aminocyclohexanols in the preparation of pharmaceutical compositions for the treatment of various indications, especially pain, as well as the treatment of these indications.

BACKGROUND OF THE INVENTION

The heptadecapeptide nociceptin is an endogenous ligand of the ORL1 (opioid receptor-like) receptor (Meunier et al., Nature 377, 1995, p. 532–535) which belongs to the family of opioid receptors and is to be found in many regions of the brain and spinal cord (Mollereau et al., FEBS Letters, 341, 1994, p. 33–38, Darland et al., Trends in Neurosciences, 21, 1998, p. 215–221). The peptide is characterized by a high affinity, with a $K_d$ value of approximately 56 pM (Ardati et al., Mol. Pharmacol. 51, p. 816–824), and by a high selectivity for the ORL1 receptor. The ORL1 receptor is homologous to the μ, κ and δ opioid receptors, and the amino acid sequence of the nociceptin peptide has a strong similarity with those of the known opioid peptides. The nociceptin-induced activation of the receptor leads to an inhibition of adenylate cyclase via coupling with $G_{i/o}$ proteins (Meunier et al., Nature 377, 1995, p. 532–535). Functional similarities of the μ, κ and δ opioid receptors with the ORL1 receptor also exist at the cellular level with respect to activation of the potassium channel (Matthes et al., Mol. Pharmacol. 50, 1996, p. 447–450; Vaughan et al., Br. J. Pharmacol. 117, 1996, p. 1609–1611) and inhibition of the L-, N- and P/Q-type calcium channels (Conner et al., Br. J. Pharmacol. 118, 1996, p. 205–207; Knoflach et al., J. Neuroscience 16, 1996, p. 6657–6664).

After intercerebroventicular administration, the nociceptin peptide shows a pronociceptive and hyperalgesic activity in various animal models (Reinscheid et al., Science 270, 1995, p. 792–794; Hara et al., Br. J. Pharmacol. 121, 1997, p. 401–408). These findings can be explained as an inhibition of stress-induced analgesia (Mogil et al., Neurosci. Letters 214, 1996, p 131–134; and Neuroscience 75, 1996, p. 333–337). It has also been possible to detect an anxiolytic activity of nociceptin in this connection (Jenck et al., Proc. Natl. Acad. Sci. USA 94, 1997, 14854–14858).

On the other hand, it has also been possible to demonstrate an antinociceptive effect of nociceptin in various animal models, in particular after intrathecal administration. Nociceptin inhibits the activity of kainate- or glutamate-stimulated posterior route ganglia neurones (Shu et al., Neuropeptides, 32, 1998, 567–571) or glutamate-stimulated spinal cord neurones (Faber et al., Br. J. Pharmacol., 119, 1996, p. 189–190); it has an antinociceptive action in the tail flick test in the mouse (King et al., Neurosci. Lett., 223, 1997, 113–116), in the flexor-reflex model in the rat (Xu et al., NeuroReport, 7, 1996, 2092–2094) and in the formalin test on the rat (Yamamoto et al., Neuroscience, 81, 1997, p. 249–254). It has also been possible to demonstrate an antinociceptive action of nociceptin in models for neuropathic pain (Yamamoto and Nozaki-Taguchi, Anesthesiology, 87, 1997), which is particularly interesting in as much as the activity of nociceptin increases after axotomy of spinal nerves. This is in contrast to conventional opioids, the activity of which decreases under these conditions (Abdulla and Smith, J. Neurosci. 18, 1998, p. 9685–9694).

The ORL1 receptor is furthermore also involved in the regulation of further physiological and pathophysiological processes. These include, inter alia, learning and memory formation (Sandin et al., Eur. J. Neurosci., 9, 1997, p. 194–197; Manabe et al., Nature, 394, 1997, p. 577–581), hearing ability (Nishi et al., EMBO J., 16, 1997, p. 1858–1864), food intake (Pomonis et al., NeuroReport, 8, 1996, p. 369–371), regulation of blood pressure (Gumusel et al., Life Sci., 60, 1997, p. 141–145; Campion and Kadowitz, Biochem. Biophys. Res. Comm., 234, 1997, p. 309–312), epilepsy (Gutiérrez et al., Abstract 536.18, Society for Neuroscience, Vol 24, 28th Ann. Meeting, Los Angeles, Nov. 7th–12th, 1998) and diuresis (Kapista et al., Life Sciences, 60, 1997, PL 15–21). An article by Calo et al. (Br. J. Pharmacol., 129, 2000, 1261–1283) gives an overview of the indications or biological processes in which the ORL1 receptor plays or with high probability could play a role. Those mentioned are, inter alia: analgesia, stimulation and regulation of food intake, influence on μ-agonists, such as morphine, treatment of withdrawal symptoms, reduction in the addiction potential of morphines, anxiolysis, modulation of motor activity, memory disorders, epilepsy; modulation of neurotransmitter secretion, especially of glutamate, serotonin and dopamine, and therefore neurodegenerative diseases; influencing of the cardiovascular system, initiation of an erection, diuresis, antinatriuresis, electrolyte balance, arterial blood pressure, water retention diseases, intestinal motility (diarrhea), relaxing effects on the respiratory tract, micturition reflex (urinary incontinence). The use of agonists and antagonists as anoretics, analgesics (also in co-administration with opioids) or nootropics is furthermore discussed.

The possible uses of compounds which bind to the ORL1 receptor and activate or inhibit it are correspondingly diverse.

SUMMARY OF THE INVENTION

One object of the present invention was to provide active ingredients which act on the nociceptin/ORL1 receptor system and are therefore suitable for pharmaceutical compositions, especially for treatment of the various diseases connected with this system according to the prior art or for use in the indications mentioned there.

The invention therefore provides substituted 4-aminocyclohexanols (called compound group A hereinbelow) corresponding to the general formula I

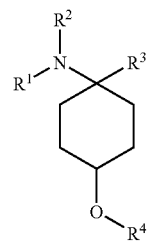

wherein

R¹ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

R² is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

the radicals R¹ and R² together form a ring and denote $CH_2CH_2OCH_2CH_2$, $CH_2CH_2NR^5CH_2CH_2$ or $(CH_2)_{3-6}$, wherein the alkyl groups may be mono- or poly-substituted, where R⁵ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

R³ is selected from $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

R⁴ is selected from $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$; or —$R^8$-L-$R^9$ where R⁶ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; or C(O)O—$R^{10}$;

where $R^{10}$ is selected from $C_{1-7}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted;

where R⁷ is selected from

H; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted, where R⁸ is selected from $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted, where L is selected from —C(O)—NH—, —NH—C(O)—, —C(O)—O—, —O—C(O)—, —O—, —S— or —S(O)₂—, where R⁹ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted, optionally in the form of their racemates, their pure stereoisomers, especially enantiomers or diastereoisomers, or in the form of mixtures of the stereoisomers, especially of the enantiomers or diastereoisomers, in any mixing ratio; in the prepared form or in the form of their acids or their bases or in the form of their salts, especially the physiologically acceptable salts, or in the form of their solvates, especially the hydrates, with the proviso that R⁴ is not $CH_3$ and when the radicals R¹ and R² together denote $(CH_2)_5$, R⁴ is not —$CH_2$-phenyl.

The invention further provides substituted 4-aminocyclohexanols (called compound group B hereinbelow) corresponding to the general formula I

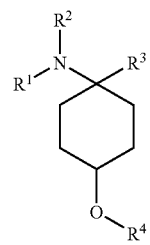

I wherein

R¹ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

R² is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

$R^3$ is selected from $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

$R^4$ is selected from $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$; or —$R^8$-L-$R^9$ where $R^6$ is selected from
  H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; or C(O)O—$R^{10}$;
  where $R^{10}$ is selected from
    $C_{1-7}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted;
where $R^7$ is selected from
  H; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted,
where $R^8$ is selected from
  $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted,
where L is selected from
  —C(O)—NH—, —NH—C(O)—, —C(O)—O—, —O—C(O)—, —O—, —S— or —S(O)$_2$—,
where $R^9$ is selected from
  H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted, optionally in the form of their racemates, their pure stereoisomers, especially enantiomers or diastereoisomers, or in the form of mixtures of the stereoisomers, especially of the enantiomers or diastereoisomers, in any mixing ratio;

in the prepared form or in the form of their acids or their bases or in the form of their salts, especially the physiologically acceptable salts, or in the form of their solvates, especially the hydrates, with the proviso that when $R^1$ and $R^2$ represent H and $R^3$ represents $CH_3$, $R^4$ is not a group of the formula

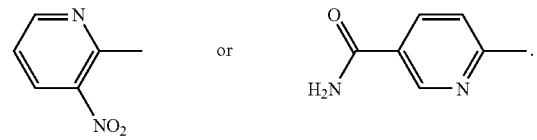

The invention further provides substituted 4-aminocyclohexanols (called compound group C hereinbelow) corresponding to the general formula II

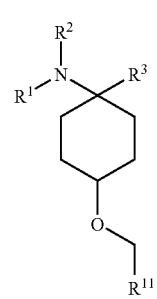

wherein $R^1$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

$R^2$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

or the radicals $R^1$ and $R^2$ together form a ring and denote $CH_2CH_2OCH_2CH_2$, $CH_2CH_2NR^5CH_2CH_2$ or $(CH_2)_{3-6}$, wherein the alkyl groups may be mono- or poly-substituted,
  where $R^5$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, in each case mono- or poly-substituted or unsubstituted;

$R^3$ is selected from $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

$R^{11}$ is selected from $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; —$CHR^6R^7$, —$CHR^6$—$CH_2R^7$, —$CHR^6$—$CH_2$—$CH_2R^7$; or —$R^8$-L-$R^9$ where $R^6$ is selected from
  H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; or $C(O)O$—$R^{10}$;
  where $R^{10}$ is selected from
    $C_{1-7}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted;
where $R^7$ is selected from
  H; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted,
where $R^8$ is selected from
  $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted,
where L is selected from
  —C(O)—NH—, —NH—C(O)—, —C(O)—O—, —O—C(O)—, —O—, —S— or —S(O)$_2$—,
where $R^9$ is selected from
  H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted,
optionally in the form of their racemates, their pure stereoisomers, especially enantiomers or diastereoisomers, or in the form of mixtures of the stereoisomers, especially of the enantiomers or diastereoisomers, in any mixing ratio; in the prepared form or in the form of their acids or their bases or in the form of their salts, especially the physiologically acceptable salts, or in the form of their solvates, especially the hydrates,
with the proviso that
when the radicals $R^1$ and $R^2$ together form a ring and denote $(CH_2)_5$,
$R^{11}$ is not phenyl.

The invention further provides substituted 4-aminocyclohexanols (called compound group D hereinbelow) according to the general formula III

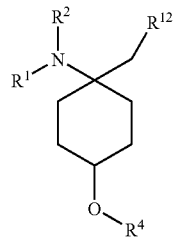

wherein
$R^1$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;
$R^2$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;
or the radicals $R^1$ and $R^2$ together form a ring and denote $CH_2CH_2OCH_2CH_2$, $CH_2CH_2NR^5CH_2CH_2$ or $(CH_2)_{3-6}$, wherein the alkyl groups may be mono- or poly-substituted,
  where $R^5$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, in each case mono- or poly-substituted or unsubstituted;
$R^{12}$ is selected from $C_{1-7}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-2}$-alkyl bridge, in each case mono- or poly-substituted or unsubstituted; or heterocyclyl bonded via a $C_{1-2}$-alkyl bridge, saturated or unsaturated, mono- or poly-substituted or unsubstituted;
$R^4$ is selected from $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; —$CHR^6R^7$, —$CHR^6$—$CH_2R^7$, —$CHR^6$—$CH_2$—$CH_2R^7$, —$CHR^6$—$CH_2$—$CH_2$—$CH_2R^7$; or —$R^8$-L-$R^9$ where $R^6$ is selected from
- H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; or C(O)O—$R^{10}$;
- where $R^{10}$ is selected from
  - $C_{1-7}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted;
- where $R^7$ is selected from
  - H; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted,
- where $R^8$ is selected from
  - $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted,
- where L is selected from
  - —C(O)—NH—, —NH—C(O)—, —C(O)—O—, —O—C(O)—, —O—, —S— or —S(O)$_2$—,
- where $R^9$ is selected from
  - H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted, optionally in the form of their racemates, their pure stereoisomers, especially enantiomers or diastereoisomers, or in the form of mixtures of the stereoisomers, especially of the enantiomers or diastereoisomers, in any mixing ratio; in the prepared form or in the form of their acids or their bases or in the form of their salts, especially the physiologically acceptable salts, or in the form of their solvates, especially the hydrates.

All these compounds and compound groups according to the invention exhibit outstanding binding to the ORL1 receptor and exhibit analgesic activity.

In the context of this invention, alkyl and cycloalkyl radicals are understood as meaning saturated and unsaturated (but not aromatic), branched, unbranched and cyclic hydrocarbons, which can be unsubstituted or mono- or poly-substituted. $C_{1-2}$-Alkyl means C1- or C2-alkyl, $C_{1-3}$-alkyl means C1-, C2- or C3-alkyl, $C_{1-4}$-alkyl means C1-, C2-, C3- or C4-alkyl, $C_{1-5}$-alkyl means C1-, C2-, C3-, C4- or C5-alkyl, $C_{1-6}$-alkyl means C1-, C2-, C3-, C4-, C5- or C6-alkyl, $C_{1-7}$-alkyl means C1-, C2-, C3-, C4-, C5-, C6- or C7-alkyl, $C_{1-8}$-alkyl means C1-, C2-, C3-, C4-, C5-, C6-, C7- or C8-alkyl, $C_{1-10}$-alkyl means C1-, C2-, C3-, C4-, C5-, C6-, C7-, C8-, C9- or C10-alkyl and $C_{1-18}$-alkyl means C1-, C2-, C3-, C4-, C5-, C6-, C7-, C8-, C9-, C10-, C 11-, C12-, C13-, C14-, C15-, C16-, C17 or C18-alkyl. Furthermore, $C_{3-4}$-cycloalkyl means C3- or C4-cycloalkyl, $C_{3-5}$-cycloalkyl means C3-, C4- or C5-cycloalkyl, $C_{3-6}$-cycloalkyl means C3-, C4-, C5- or C6-cycloalkyl, $C_{3-7}$-cycloalkyl means C3-, C4-, C5-, C6- or C7-cycloalkyl, $C_{3-8}$-cycloalkyl means C3-, C4-, C5-, C6-, C7 or C8-cycloalkyl, $C_{4-5}$-cycloalkyl means C4- or C5-cycloalkyl, $C_{4-6}$-cycloalkyl means C4-, C5- or C6-cycloalkyl, $C_{4-7}$-cycloalkyl means C4-, C5-, C6- or C7-cycloalkyl, $C_{5-6}$-cycloalkyl means C5- or C6-cycloalkyl and $C_{5-7}$-cycloalkyl means C5-, C6- or C7-cycloalkyl. In respect of cycloalkyl, the term also includes saturated cycloalkyls in which one or 2 carbon atoms are replaced by a heteroatom, S, N or O. However, the term cycloalkyl also includes especially mono- or poly-unsaturated, preferably monounsaturated, cycloalkyls without a heteroatom in the ring, provided the cycloalkyl is not an aromatic system. The alkyl and cycloalkyl radicals are preferably methyl, ethyl, vinyl (ethenyl), propyl, allyl (2-propenyl), 1-propinyl, methylethyl,(butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl, $CHF_2$, $CF_3$ or $CH_2OH$, as well as pyrazolinone, oxopyrazolinone, [1,4]dioxane or dioxolane.

In connection with alkyl and cycloalkyl—unless expressly defined otherwise—the term substituted here is understood in the context of this invention as meaning the substitution of a hydrogen radical by F, Cl, Br, I, $NH_2$, SH or OH, where "polysubstituted" is to be understood as meaning that the substitution occurs several times with the same or different substituents both on different and on the same atoms, for example three times on the same C atom, as in the case of $CF_3$, or at different places, as in the case of —CH(OH)—CH=CH—$CHCl_2$. Particularly preferred substituents here are F, Cl and OH.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—, etc.

An aryl radical is understood as meaning ring systems having at least one aromatic ring but without heteroatoms in even only one of the rings. Examples are phenyl, naphthyl, fluoranthenyl, fluorenyl, tetralinyl or indanyl, especially 9H-fluorenyl or anthracenyl radicals, which can be unsubstituted or mono- or poly-substituted.

A heteroaryl radical is understood as meaning heterocyclic ring systems having at least one unsaturated ring, which contain one or more heteroatoms from the group nitrogen, oxygen and/or sulfur and can also be mono- or poly-substituted. Examples which may be mentioned from the group of heteroaryls are furan, benzofuran, thiophene, benzothiophene, pyrrole, pyridine, pyrimidine, pyrazine, quinoline, isoquinoline, phthalazine, benzo[1,2,5]-thiadiazole, benzothiazole, indole, benzotriazole, benzodioxolane, benzodioxane, carbazole, indole and quinazoline.

In connection with aryl and heteroaryl, substituted here is understood as meaning—unless expressly defined otherwise—substitution of the aryl or heteroaryl with $R^{23}$, $OR^{23}$ a halogen, preferably F and/or Cl, a $CF_3$, a CN, an $NO_2$, an $NR^{24}R^{25}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

The radical $R^{23}$ here represents H, a $C_{1-10}$-alkyl radical, preferably a $C_{1-6}$-alkyl radical, an aryl or heteroaryl radical or an aryl or heteroaryl radical bonded via a $C_{1-3}$-alkylene group, wherein these aryl and heteroaryl radicals may not themselves be substituted by aryl or heteroaryl radicals, the radicals $R^{24}$ and $R^{25}$, which are identical or different, represent H, a $C_{1-10}$-alkyl radical, preferably a $C_{1-6}$-alkyl radical, an aryl radical, a heteroaryl radical or an aryl or heteroaryl radical bonded via a $C_{1-3}$-alkylene group, wherein these aryl and heteroaryl radicals may not themselves be substituted by aryl or heteroaryl radicals, or the radicals $R^{24}$ and $R^{25}$ together represent $CH_2CH_2OCH_2CH_2$, $CH_2CH_2NR^{26}CH_2CH_2$ or $(CH_2)_{3-6}$, and the radical $R^{26}$ represents H, a $C_{1-10}$-alkyl radical, preferably a $C_{1-6}$-alkyl radical, an aryl or heteroaryl radical or an aryl or heteroaryl radical bonded via a $C_{1-3}$-alkylene group, wherein these aryl and heteroaryl radicals may not themselves be substituted by aryl or heteroaryl radicals.

The term salt is understood as meaning any form of the active ingredient according to the invention in which the active ingredient assumes an ionic form or is charged and is coupled with a counter-ion (a cation or anion) or is in solution. The term is also understood as meaning complexes of the active ingredient with other molecules and ions, especially complexes complexed via ionic interactions.

The term of the physiologically acceptable salt with cations or bases is understood in the context of this invention as meaning salts of at least one of the compounds according to the invention—in most cases of a (deprotonated) acid—as the anion with at least one cation, preferably an inorganic cation, which are physiologically acceptable—especially when used in humans and/or mammals. The salts of the alkali metals and alkaline earth metals and also $NH_4^+$ are particularly preferred, but especially (mono-) or (di-)sodium, (mono-) or (di-)potassium, magnesium or calcium salts.

The term of the physiologically acceptable salt with anions or acids is understood in the context of this invention as meaning salts of at least one of the compounds according to the invention—in most cases protonated, for example at the nitrogen—as the cation with at least one anion, which are physiologically acceptable—especially when used in humans and/or mammals. In particular, the term is understood in the context of this invention as meaning the salt formed with a physiologically acceptable acid, namely salts of the particular active ingredient with inorganic or organic acids, which are physiologically acceptable—especially when used in humans and/or mammals. Examples of physiologically acceptable salts of particular acids are salts of: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydrolb6-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, a-liponic acid, acetylglycine, acetylsalicylic acid, hippuric acid and/or aspartic acid. The hydrochloride salt is particularly preferred.

For compound groups C or D, particular preference is given to substituted 4-aminocyclohexanols in which
$R^1$ is selected from $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;
$R^2$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

For compound group A, particular preference is given to substituted 4-aminocyclohexanols in which or the radicals $R^1$ and $R^2$ together form a ring and denote $CH_2CH_2OCH_2CH_2$, $CH_2CH_2NR^5CH_2CH_2$ or $(CH_2)_{3-6}$, wherein the alkyl groups may be mono- or poly-substituted,
where $R^5$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, in each case mono- or poly-substituted or unsubstituted.

It is particularly preferred (for compound groups C or D) if
$R^1$ is selected from $C_{1-8}$-alkyl, saturated or unsaturated, branched or unbranched, mono- or poly-substituted or unsubstituted;
$R^2$ is selected from H; $C_{1-8}$-alkyl, saturated or unsaturated, branched or unbranched, mono- or poly-substituted or unsubstituted;

and (for compound group A) if
the radicals $R^1$ and $R^2$ together form a ring and denote $CH_2CH_2OCH_2CH_2$, $CH_2CH_2NR^5CH_2CH_2$ or $(CH_2)_{3-6}$,
where $R^5$ is selected from H; $C_{1-8}$-alkyl, saturated or unsaturated, branched or unbranched, mono- or poly-substituted or unsubstituted, preferably (for compound groups C or D)
$R^1$ is selected from $C_{1-4}$-alkyl, saturated or unsaturated, branched or unbranched, mono- or poly-substituted or unsubstituted; where $R^1$ and $R^2$ may not both be H,
$R^2$ is selected from H; $C_{1-4}$-alkyl, saturated or unsaturated, branched or unbranched, mono- or poly-substituted or unsubstituted;

and (for compound group A)
the radicals $R^1$ and $R^2$ together form a ring and denote $(CH_2)_{4-5}$, especially (for compound groups C or D)
$R^1$ and $R^2$ represent methyl.

For compound group B, particular preference is given to substituted 4-aminocyclohexanols in which
$R^1$ is selected from $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted; and
$R^2$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted.

It is particularly preferred (for compound group B) if
$R^1$ is selected from $C_{1-8}$-alkyl, saturated or unsaturated, branched or unbranched, mono- or poly-substituted or unsubstituted;
$R^2$ is selected from H; $C_{1-8}$-alkyl, saturated or unsaturated, branched or unbranched, mono- or poly-substituted or unsubstituted;

preferably
$R^1$ is selected from $C_{1-4}$-alkyl, saturated or unsaturated, branched or unbranched, mono- or poly-substituted or unsubstituted; where $R^1$ and $R^2$ may not both be H,
$R^2$ is selected from H; $C_{1-4}$-alkyl, saturated or unsaturated, branched or unbranched, mono- or poly-substituted or unsubstituted;

especially
$R^1$ and $R^2$ represent methyl.

For compound groups C or D, particular preference is given to substituted 4-aminocyclohexanols in which
$R^1$ is selected from H; $C_{1-8}$-alkyl, saturated or unsaturated, branched or unbranched, mono- or poly-substituted or unsubstituted;
$R^2$ is selected from H; $C_{1-8}$-alkyl, saturated or unsaturated, branched or unbranched, mono- or poly-substituted or unsubstituted;

and for compound group A substituted 4-aminocyclohexanols in which
the radicals $R^1$ and $R^2$ together form a ring and denote $CH_2CH_2OCH_2CH_2$, $CH_2CH_2NR^5CH_2CH_2$ or $(CH_2)_{3-6}$, where $R^5$ is selected from H; $C_{1-8}$-alkyl, saturated or unsaturated, branched or unbranched, mono- or poly-substituted or unsubstituted, preferably for compound groups C or D
$R^1$ is selected from H; $C_{1-4}$-alkyl, saturated or unsaturated, branched or unbranched, mono- or poly-substituted or unsubstituted; where $R^1$ and $R^2$ may not both be H,
$R^2$ is selected from H; $C_{1-4}$-alkyl, saturated or unsaturated, branched or unbranched, mono- or poly-substituted or unsubstituted;

and for compound group A
the radicals $R^1$ and $R^2$ together form a ring and denote $(CH_2)_{4-5}$, especially (for compound groups C or D)
$R^1$ and $R^2$ represent methyl.

For compound group B, particular preference is given to substituted 4-aminocyclohexanols in which
$R^1$ is selected from H; $C_{1-8}$-alkyl, saturated or unsaturated, branched or unbranched, mono- or poly-substituted or unsubstituted;
$R^2$ is selected from H; $C_{1-8}$-alkyl, saturated or unsaturated, branched or unbranched, mono- or poly-substituted or unsubstituted;

preferably
$R^1$ is selected from H; $C_{1-4}$-alkyl, saturated or unsaturated, branched or unbranched, mono- or poly-substituted or unsubstituted; where $R^1$ and $R^2$ may not both be H,
$R^2$ is selected from H; $C_{1-4}$-alkyl, saturated or unsaturated, branched or unbranched, mono- or poly-substituted or unsubstituted;

especially
$R^1$ and $R^2$ represent methyl.

For compound groups A, B or C, particular preference is given to substituted 4-aminocyclohexanols in which
$R^3$ is selected from $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, in each case mono- or poly-substituted or unsubstituted;

preferably
$R^3$ is selected from $C_{5-6}$-cycloalkyl, unsubstituted or mono- or poly-substituted; phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, in each case unsubstituted or mono- or poly-substituted, or $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched $C_{1-2}$-alkyl group, in each case unsubstituted or mono- or poly-substituted;

especially
$R^3$ is selected from phenyl, pyridyl, furyl or thiophenyl, in each case unsubstituted or mono- or poly-substituted; or phenyl, pyridyl, furyl or thiophenyl bonded via a saturated, unbranched $C_{1-2}$-alkyl group, in each case unsubstituted or mono- or poly-substituted.

For compound group D, particular preference is given to substituted 4-aminocyclohexanols in which
$R^{12}$ is selected from $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-2}$-alkyl bridge, in each case mono or poly-substituted or unsubstituted; or heterocyclyl bonded via a $C_{1-2}$-alkyl bridge, saturated or unsaturated, in each case mono- or poly-substituted or unsubstituted;

preferably
$R^{12}$ is selected from $C_{5-6}$-cycloalkyl, unsubstituted or mono- or poly-substituted; phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, in each case unsubstituted or mono- or poly-substituted, or $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a $CH_2$ group, in each case unsubstituted or mono- or poly-substituted;

especially
$R^{12}$ is selected from phenyl, pyridyl, furyl or thiophenyl, in each case unsubstituted or mono- or poly-substituted; or phenyl, pyridyl, furyl or thiophenyl bonded via a saturated, unbranched $CH_2$ group, in each case unsubstituted or mono- or poly-substituted.

For compound groups A, B or D, particular preference is given to substituted 4-aminocyclohexanols in which $R^4$ is selected from $C_{3-8}$-cycloalkyl, aryl or heteroaryl, in each case unsubstituted or mono- or poly-substituted; or —$R^8$-L-$R^9$, preferably $R^4$ is selected from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or poly-substituted; or —$R^8$-L-$R^9$, especially $R^4$ is selected from cyclopentyl, cyclohexyl, cycloheptyl, cyclooctyl, anthracenyl, indolyl, naphthyl, benzothiazolyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or poly-substituted; or —$R^8$-L-$R^9$.

For compound group C, particular preference is given to substituted 4-aminocyclohexanols in which $R^{11}$ is selected from $C_{3-8}$-cycloalkyl, aryl or heteroaryl, in each case unsubstituted or mono- or poly-substituted; or —$R^8$-L-$R^9$, preferably $R^{11}$ is selected from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or poly-substituted; or —$R^8$-L-$R^9$, especially $R^{11}$ is selected from cyclopentyl, cyclohexyl, cycloheptyl, cyclooctyl, anthracenyl, indolyl, naphthyl, benzothiazolyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or poly-substituted; or —$R^8$-L-$R^9$.

For the two preferred embodiments described above (for compound groups A, B or D and C), it is advantageous if $R^8$ is selected from indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl, in each case unsubstituted or mono- or poly-substituted, L is selected from
—C(O)—NH—, —NH—C(O)—, —C(O)—O—, —O—C(O)—, —O—, —S— or —S(O)$_2$, and/or $R^9$ is selected from indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl or quinazolinyl, in each case unsubstituted or mono- or poly-substituted, preferably $R^8$ is selected from indolyl, benzothiophenyl, phenyl, thiophenyl, furyl, pyridyl, pyrrolyl, pyrazinyl or pyrimidyl, in each case unsubstituted or mono- or poly-substituted, L is selected from
—C(O)—NH—, —NH—C(O)—, —C(O)—O—, —O—C(O)— or —S(O)$_2$—, and/or $R^9$ is selected from indolyl, benzothiophenyl, phenyl, thiophenyl, furyl, pyridyl, pyrrolyl, pyrazinyl or pyrimidyl, in each case unsubstituted or mono- or poly-substituted, especially $R^8$ is selected from
indolyl, unsubstituted, L is selected from
—S(O)$_2$— and $R^9$ is selected from
phenyl, unsubstituted.

For compound groups A, B and D, particular preference is given to substituted 4-aminocyclohexanols in which $R^4$ is selected from —CH$^6$R$^7$, —CHR$^6$—CH$_2$R$^7$, —CHR$^6$—CH$_2$—CH$_2$R$^7$, —CHR$^6$—CH$_2$—CH$_2$R$^7$, preferably $R^4$ is selected from —CHR$^6$R$^7$, —CHR$^6$—CH$_2$R$^7$ or —CHR$^6$—CH$_2$—CH$_2$R$^7$, especially $R^4$ is selected from —CHR$^6$R$^7$ or —CHR$^6$—CH$_2$R$^7$.

For compound group B, particular preference is given to substituted 4-aminocyclohexanols in which $R^{11}$ is selected from —CHR$^6$R$^7$, —CHR$^6$—CH$_2$R$^7$ or —CHR$^6$—CH$_2$—CH$_2$R$^7$, preferably $R^{11}$ is selected from —CHR$^6$R$^7$ or —CHR$^6$—CH$_2$R$^7$, especially $R^{11}$ is selected from —CHR$^6$R$^7$.

For the two preferred embodiments described above (for compound groups A, B or D and C), it is advantageous if $R^6$ is selected from H, $C_{1-4}$-alkyl, saturated or unsaturated, branched or unbranched, mono- or poly-substituted or unsubstituted; or C(O)OR$^{10}$ where $R^{10}$ is selected from $C_{1-4}$-alkyl, saturated or unsaturated, branched or unbranched, mono- or poly-substituted or unsubstituted;

preferably

H, $C_{1-4}$-alkyl, saturated or unsaturated, branched or unbranched, mono- or poly-substituted or unsubstituted;

especially

H, CH$_3$ and C$_2$H$_5$.

For the three preferred embodiments described above (for compound groups A, B or D and C), it is advantageous if R$^7$ is selected from C$_{3-8}$-cycloalkyl, aryl or heteroaryl, in each case unsubstituted or mono- or poly-substituted;

preferably

R$^7$ is selected from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or poly-substituted;

especially

R$^7$ is selected from cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or poly-substituted.

The substituted 4-aminocyclohexanols according to the invention are particularly preferably selected from the following group:

trans-(4-benzyloxy-1-phenylcyclohexyl)dimethylamine
cis-(4-benzyloxy-1-phenylcyclohexyl)dimethylamine
trans-(1-benzyl-4-benzyloxycyclohexyl)dimethylamine
cis-(1-benzyl-4-benzyloxycyclohexyl)dimethylamine
trans-[4-benzyloxy-1-(2-methylbenzyl)cyclohexyl]dimethylamine
cis-[4-benzyloxy-1-(2-methylbenzyl)cyclohexyl]dimethylamine
cis-[4-(2-fluorobenzyloxy)-1-phenylcyclohexyl]dimethylamine
cis-[1-benzyl-4-(3-fluorobenzyloxy)cyclohexyl]dimethylamine
cis-[1-benzyl-4-(2-fluorobenzyloxy)cyclohexyl]dimethylamine
cis-[1-benzyl-4-(4-fluorobenzyloxy)cyclohexyl]dimethylamine
trans-[4-(2-fluorobenzyloxy)-1-phenylcyclohexyl]dimethylamine
trans-[4-(3-fluorobenzyloxy)-1-phenylcyclohexyl]dimethylamine
trans-[4-(4-fluorobenzyloxy)-1-phenylcyclohexyl]dimethylamine
trans-[4-(4-fluorobenzyloxy)-1-phenethylcyclohexyl]dimethylamine
trans-[4-(3-fluorobenzyloxy)-1-phenethylcyclohexyl]dimethylamine
(1H-indol-3-yl)-acetic acid 4-dimethylamino-4-phenyl-cyclohexyl ester optionally in the form of their racemates, of their pure stereoisomers, especially enantiomers or diastereoisomers, or in the form of mixtures of the stereoisomers, especially of the enantiomers or diastereoisomers, in any mixing ratio;

in the prepared form or in the form of their acids or their bases or in the form of their salts, especially the physiologically acceptable salts, or in the form of their solvates, especially the hydrates.

The substances according to the invention are toxicologically harmless, so that they are suitable as a pharmaceutical active ingredients in pharmaceutical compositions. The invention further provides pharmaceutical compositions comprising at least one 4-aminocyclohexanol according to the invention, optionally in the form of its racemate, its pure stereoisomers, especially enantiomers or diastereoisomers, or in the form of mixtures of the stereoisomers, especially of the enantiomers or diastereoisomers, in any mixing ratio; in the prepared form or in the form of its acids or its bases or in the form of its salts, especially the physiologically acceptable salts, or in the form of its solvates, especially the hydrates, and also, optionally, suitable additives and/or auxiliary substances and/or, optionally, further active ingredients.

In addition to at least one substituted 4-aminocyclohexanol according to the invention, the pharmaceutical composition may also preferably comprises an opioid, preferably a strong opioid, especially morphine, or an anaesthetic, preferably hexobarbital or halothane.

In addition to at least one 4-aminocyclohexanol according to the invention, the pharmaceutical compositions according to the invention optionally comprise suitable additives and/or auxiliary substances, that is to say also carriers, fillers, solvents, diluents, colourings and/or binders, and can be administered as liquid forms in the form of injection solutions, drops or juices, as semi-solid forms in the form of granules, tablets, pellets, patches, capsules, plasters or aerosols. The choice of the auxiliary substances etc. and the amounts thereof to be employed depend on whether the pharmaceutical composition is to be administered orally, perorally, parenterally, intravenously, intraperitoneally, intradermally, intramuscularly, intranasally, buccally, rectally or locally, for example to the skin, the mucous membranes or in the eyes. Formulations in the form of tablets, dragees, capsules, granules, drops, juices and syrups are suitable for oral administration, solutions, suspensions, readily reconstitutable dry formulations and sprays are suitable for parenteral and topical administration and for administration by inhalation. 4-Aminocyclohexanols according to the invention in a depot, in dissolved form or in a plaster, optionally with the addition of agents which promote penetration through the skin, are suitable formulations for percutaneous administration. Preparation forms which can be used orally or percutaneously can release the 4-aminocyclohexanols according to the invention in a delayed manner. Other further active ingredients known to the person skilled in the art can in principle be added to the pharmaceutical compositions according to the invention.

The amount of active ingredient to be administered to the patients varies in dependence on the weight of the patient, the mode of administration, the indication and the severity of the disease. From 0.005 to 1000 mg/kg, preferably from 0.05 to 5 mg/kg, of at least one 4-aminocyclohexanol according to the invention are conventionally administered. ingredients known to the person skilled in the art can in principle be added to the pharmaceutical compositions according to the invention.

The amount of active ingredient to be administered to the patients varies in dependence on the weight of the patient, the mode of administration, the indication and the severity of the disease. From 0.005 to 1000 mg/kg, preferably from 0.05 to 5 mg/kg, of at least one 4-aminocyclohexanol according to the invention are conventionally administered.

The invention relates further to the use of a substituted 4-aminocyclohexanol according to the invention, optionally in the form of its racemates, its pure stereoisomers, especially enantiomers or diastereoisomers, or in the form of mixtures of the stereoisomers, especially of the enantiomers or diastereoisomers, in any mixing ratio; in the prepared form or in the form of its acids or its bases or in the form of its salts, especially the physiologically acceptable salts, or in the form of its solvates, especially the hydrates, in the preparation of a pharmaceutical composition for the treatment of pain, especially of acute neuropathic or chronic pain.

The invention also relates further to the use of a substituted 4-aminocyclohexanol according to the invention, optionally in the form of its racemates, its pure stereoisomers, especially enantiomers or diastereoisomers, or in the form of mixtures of the stereoisomers, especially of the enantiomers or diastereoisomers, in any mixing ratio; in the prepared form or in the form of its acids or its bases or in the form of its salts, especially the physiologically acceptable salts, or in the form of its solvates, especially the hydrates, in the preparation of a pharmaceutical composition for the treatment of anxiety, stress and syndromes associated with stress, depression, epilepsy, Alzheimer's disease, senile dementia, general cognitive dysfunctions, learning and memory difficulties (as a nootropic agent), withdrawal symptoms, alcohol and/or drug and/or pharmaceutical composition or substance abuse and/or dependency, sexual dysfunctions, cardiovascular diseases, hypotension, hypertension, tinnitus, pruritus, migraine, impaired hearing, deficient intestinal motility, impaired food intake, anorexia, obesity, locomotor disorders, diarrhea, cachexia, urinary incontinence or as a muscle relaxant, anticonvulsive or anaesthetic or for co-administration on treatment with an opioid analgesic or with an anaesthetic, for diuresis or antinatriuresis and/or anxiolysis.

The invention accordingly further provides a process for the preparation of a substituted 4-aminocyclohexanol according to the invention of compound group A, comprising the following steps:

a. a cyclohexane-1,4-dione, protected with groups $S^1$ and $S^2$, according to formula IV is reacted with a cyanide, preferably potassium cyanide, in the presence of a compound of the formula $HNR^{01}R^{02}$ to give a protected N-substituted 1-amino-4-oxo-cyclohexanecarbonitrile derivative according to formula V;

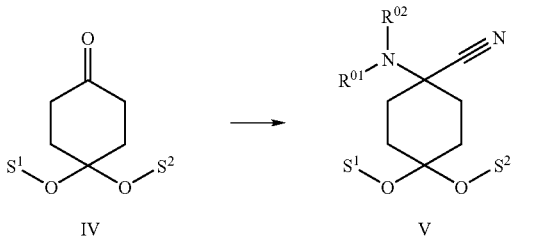

IV           V acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, b. the aminonitrile according to formula V is reacted with organometallic reagents, preferably Grignard or organolithium reagents, of the formula metal-$R^3$, so that a compound according to formula VI is formed;

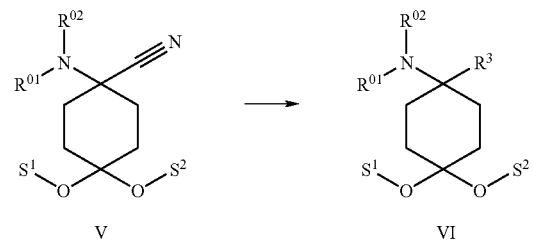

V           VI acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, c. on the compound according to formula VI, the protecting groups $S^1$ and $S^2$ are split off, so that a 4-substituted 4-aminocyclohexanone derivative according to formula VII is formed;

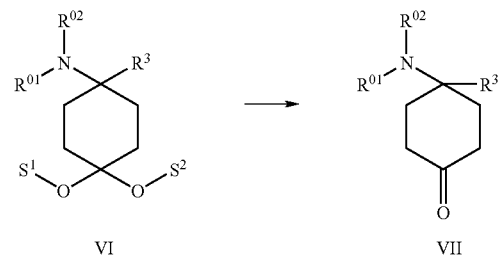

VI           VII acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, d. the 4-substituted 4-aminocyclohexanone derivative according to formula VII is reacted with a reducing agent such as, for example, sodium borohydride, sodium cyanoborohydride, sodium triacetoxyborohydride, lithium aluminium hydride, diisobutylaluminium hydride, a complex analogue of these compounds, at temperatures of from $-70°$ C. to $+110°$ C., or with noble metal catalysis with hydrogen, to give a 4-aminocyclohexanol derivative according to formula VIII;

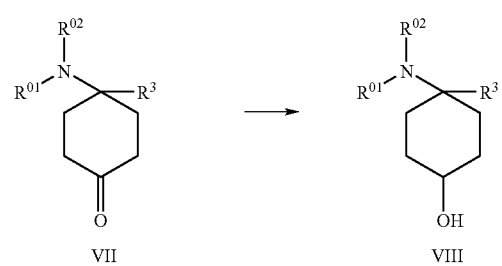

VII           VIII e. the 4-substituted 4-aminocyclohexanol derivative according to formula VIII is then reacted in the presence of an inorganic, organometallic or organic base with an alkyl, acyl or aryl bromide, chloride, iodide or triflate or with an alkane, alkyl acid or aromatic compound $R^4X$ provided with a different leaving group X to give a compound according to formula I, wherein $R^1$, $R^2$, $R^3$ and $R^4$ are as defined for compound group A and the radicals $R^{01}$ and $R^{02}$ together form a ring and denote $CH_2CH_2OCH_2CH_2$, $CH_2CH_2NR^{06}CH_2CH_2$ or $(CH_2)_{3-6}$.

The invention further provides a process for the preparation of a substituted 4-aminocyclohexanol according to the invention of compound group B, comprising the following steps:

a. a cyclohexane-1,4-dione, protected with groups $S^1$ and $S^2$, according to formula IV is reacted with a cyanide, preferably potassium cyanide, in the presence of a compound of the formula $HNR^{01}R^{02}$ to give a protected N-substituted 1-amino-4-oxo-cyclohexanecarbonitrile derivative according to formula V;

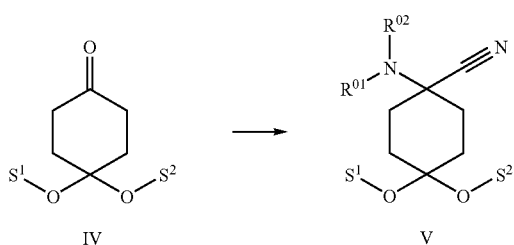

IV     V acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, b. the aminonitrile according to formula V is reacted with organometallic reagents, preferably Grignard or organolithium reagents, of the formula metal-$R^3$, so that a compound according to formula VI is formed;

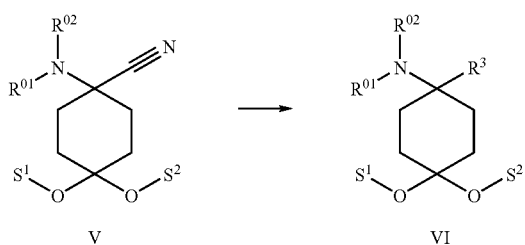

V     VI acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, c. on the compound according to formula VI, the protecting groups $S^1$ and $S^2$ are split off, so that a 4-substituted 4-aminocyclohexanone derivative according to formula VII is formed;

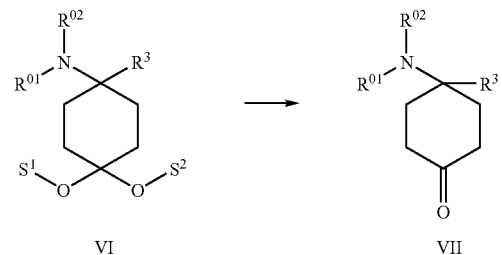

VI     VII acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, d. the 4-substituted 4-aminocyclohexanone derivative according to formula VII is reacted with a reducing agent such as, for example, sodium borohydride, sodium cyanoborohydride, sodium triacetoxyborohydride, lithium aluminium hydride, diisobutylaluminium hydride, a complex analogue of these compounds, at temperatures of from −70° C. to +110° C., or with noble metal catalysis with hydrogen, to give a 4-aminocyclohexanol derivative according to formula VIII;

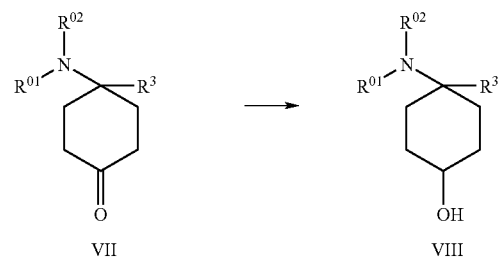

VII     VIII e. the 4-substituted 4-aminocyclohexanol derivative according to formula VIII is then reacted in the presence of an inorganic, organometallic or organic base with an alkyl, acyl or aryl bromide, chloride, iodide or triflate or with an alkane, alkyl acid or aromatic compound $R^4X$ provided with a different leaving group X to give a compound according to formula I, wherein $R^1$, $R^2$, $R^3$ and $R^4$ are as defined for compound group B and $R^{01}$ and $R^{02}$ are selected independently of one another from H; H provided with a protecting group; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkylene, in each case mono- or poly-substituted or unsubstituted.

The invention further provides a process for the preparation of a substituted 4-aminocyclohexanol according to the invention of compound group C, comprising the following steps:

a. a cyclohexane-1,4-dione, protected with groups $S^1$ and $S^2$, according to formula IV is reacted with a cyanide, preferably potassium cyanide, in the presence of a compound of the formula $HNR^{01}R^{02}$ to give a protected N-substituted 1-amino-4-oxo-cyclohexanecarbonitrile derivative according to formula V;

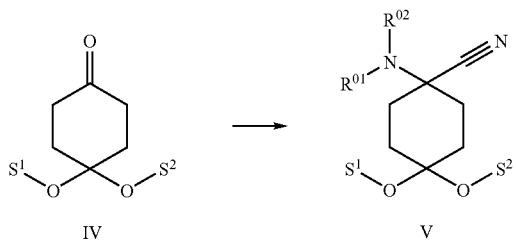

acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, b. the aminonitrile according to formula V is reacted with organometallic reagents, preferably Grignard or organolithium reagents, of the formula metal-$R^3$, so that a compound according to formula VI is formed;

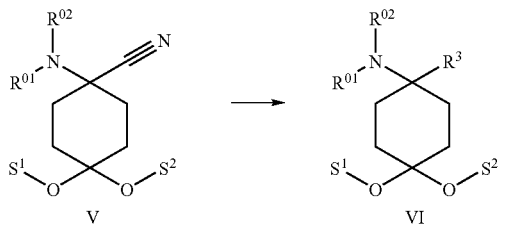

acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, c. on the compound according to formula VI, the protecting groups $S^1$ and $s^2$ are split off, so that a 4-substituted 4-aminocyclohexanone derivative according to formula VII is formed;

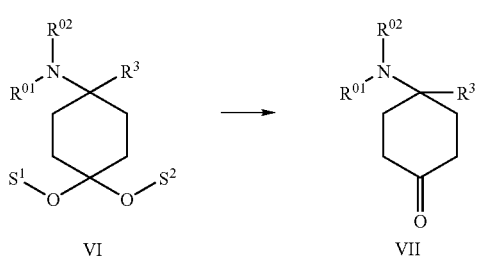

acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, d. the 4-substituted 4-aminocyclohexanone derivative according to formula VII is reacted with a reducing agent such as, for example, sodium borohydride, sodium cyanoborohydride, sodium triacetoxyborohydride, lithium aluminium hydride, diisobutylaluminium hydride, a complex analogue of these compounds, at temperatures of from −70° C. to +110° C., or with noble metal catalysis with hydrogen, to give a 4-aminocyclohexanol derivative according to formula VIII;

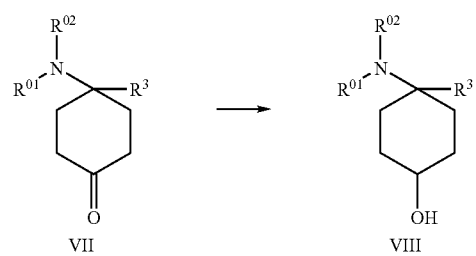

e. the 4-substituted 4-aminocyclohexanol derivative according to formula VIII is then reacted in the presence of an inorganic, organometallic or organic base with an alkyl-methyl, acyl-methyl or aryl-methyl bromide, chloride, iodide or triflate or with an alkane-methyl, alkyl acid methyl or methyl aromatic compound of the formula $R^{11}$—$CH_2$—X provided with a different leaving group X to give a compound according to formula II, wherein $R^1$, $R^2$, $R^3$ and $R^{11}$ are as defined for compound group C and $R^{01}$ and $R^{02}$ are selected independently of one another from H; H provided with a protecting group; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkylene, in each case mono- or poly-substituted or unsubstituted;

or the radicals $R^{01}$ and $R^{02}$ together form a ring and denote $CH_2CH_2OCH_2CH_2$, $CH_2CH_2NR^{06}CH_2CH_2$ or $(CH_2)_{3-6}$.

The invention further provides a process for the preparation of a substituted 4-aminocyclohexanol according to the invention of compound group D, comprising the following steps:

a. a cyclohexane-1,4-dione, protected with groups $S^1$ and $S^2$, according to formula IV is reacted with a cyanide, preferably potassium cyanide, in the presence of a compound of the formula $HNR^{01}R^{02}$ to give a protected N-substi tuted 1-amino-4-oxo-cyclohexanecarbonitrile derivative according to formula V;

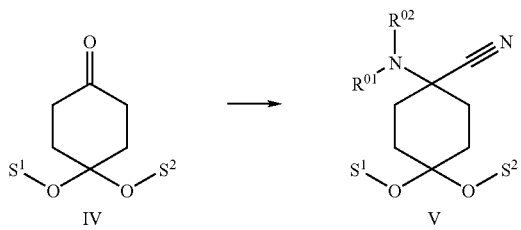

acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, b. the aminonitrile according to formula V is reacted with organometallic reagents, preferably Grignard or organolithium reagents, of the formula metal-$CH_2$—$R^{12}$, so that a compound according to formula IX is formed;

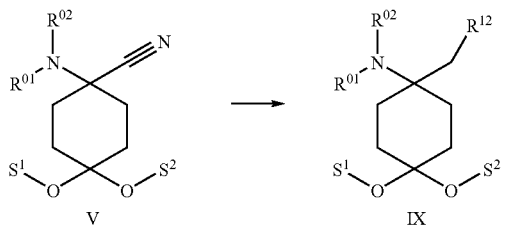

acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, c. on the compound according to formula IX, the protecting groups $S^1$ and $S^2$ are split off, so that a 4-substituted 4-aminocyclohexanone derivative according to formula XI is formed;

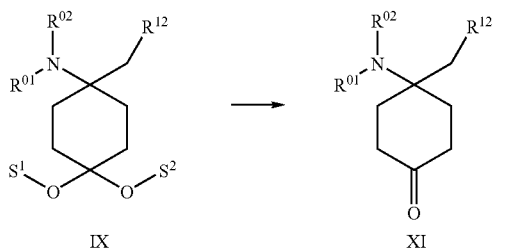

acylation, alkylation or sulfonation is then optionally carried out in any desired sequence and optionally repeatedly, and/or in the case of compounds where $R^{01}$ and/or $R^{02}$=H protected with a protecting group, a protecting group is split off at least once and acylation, alkylation or sulfonation is optionally carried out and/or in the case of compounds where $R^{01}$ and/or $R^{02}$=H, a protecting group is introduced at least once and acylation, alkylation or sulfonation is optionally carried out, d. the 4-substituted 4-aminocyclohexanone derivative according to formula XI is reacted with a reducing agent such as, for example, sodium borohydride, sodium cyanoborohydride, sodium triacetoxyborohydride, lithium aluminium hydride, diisobutylaluminium hydride, a complex analogue of these compounds, at temperatures of from −70° C. to +110° C., or with noble metal catalysis with hydrogen, to give a 4-aminocyclohexanol derivative according to formula XII;

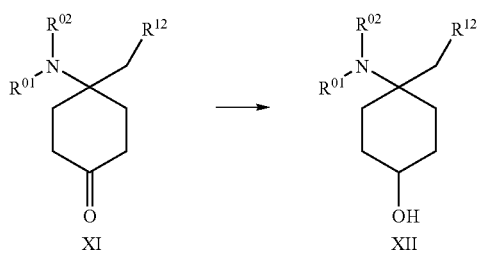

e. the 4-substituted 4-aminocyclohexanol derivative according to formula XII is then reacted in the presence of an inorganic, organometallic or organic base with an alkyl, acyl or aryl bromide, chloride, iodide or triflate or with an alkane, alkyl acid or aromatic compound $R^4X$ provided with a different leaving group X to give a compound according to formula III, wherein $R^1$, $R^2$, $R^{12}$ and $R^4$ are as defined for compound group D and $R^{01}$ and $R^{02}$ are selected independently of one another from H; H provided with a protecting group; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkylene, in each case mono- or poly-substituted or unsubstituted;

or the radicals $R^{01}$ and $R^{02}$ together form a ring and denote $CH_2CH_2OCH_2CH_2$, $CH_2CH_2NR^{06}CH_2CH_2$ or $(CH_2)_{3-6}$.

The invention further provides an alternative process for the preparation of the 4-aminocyclohexanols according to the invention of compound group A, comprising the following steps:

a. a cyclohexane-1,4-dione, protected with groups $S^1$ and $S^2$, according to formula IV is reacted with a reducing agent such as, for example, sodium borohydride, sodium cyanoborohydride, sodium triacetoxyborohydride, lithium aluminium hydride, diisobutylaluminium hydride, a complex analogue of these compounds, at temperatures of from −70° C. to +110° C., or with noble metal catalysis with hydrogen, to give a protected 4-hydroxycyclohexanone derivative according to formula XIII;

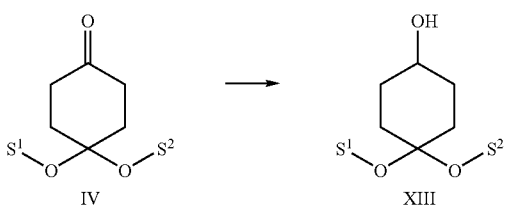

b. which is then reacted in the presence of an inorganic, organometallic or organic base with an alkyl, acyl or aryl bromide, chloride, iodide or triflate or with an alkane, carboxylic acid or aromatic compound $R^4X$ provided with a different leaving group X, to give a compound according to formula XIV;

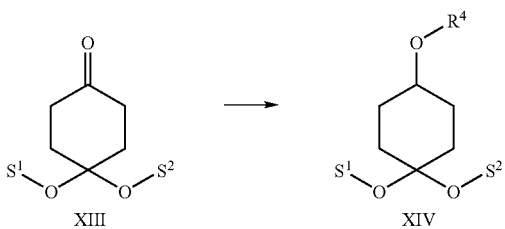

c. on the compound according to formula XIV, the protecting groups $S^1$ and $S^2$ are split off, so that a compound according to formula XV is formed;

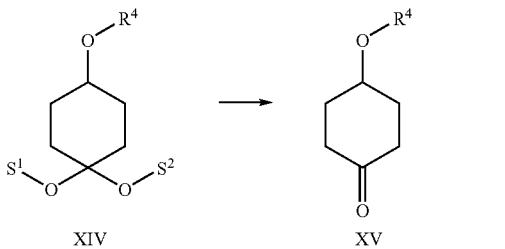

d. the compound of formula XV is reacted with cyanide, preferably potassium cyanide, in the presence of a compound of the formula $HNR^{O1}R^{O2}$ to give an α-aminonitrile derivative of formula XVI;

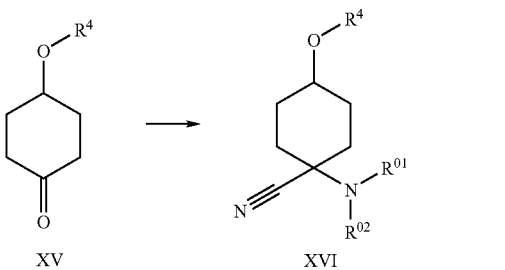

e. the aminonitrile derivative of formula XVI is reacted with organometallic reagents, preferably Grignard or organolithium reagents, of the formula metal-$R^3$ to give a compound according to formula I,
wherein $R^1$, $R^2$, $R^3$ and $R^4$ are as defined for compound group A and
the radicals $R^{O1}$ and $R^{O2}$ together form a ring and denote $CH_2CH_2OCH_2CH_2$, $CH_2CH_2NR^{O6}CH_2CH_2$ or $(CH_2)_{3-6}$.

The invention further provides an alternative process for the preparation of the 4-aminocyclohexanols according to the invention of compound group B, comprising the following steps:

a. a cyclohexane-1,4-dione, protected with groups $S^1$ and $S^2$, according to formula IV is reacted with a reducing agent such as, for example, sodium borohydride, sodium cyanoborohydride, sodium triacetoxyborohydride, lithium aluminium hydride, diisobutylaluminium hydride, a complex analogue of these compounds, at temperatures of from −70° C. to +110° C., or with noble metal catalysis with hydrogen, to give a protected 4-hydroxycyclohexanone derivative according to formula XIII;

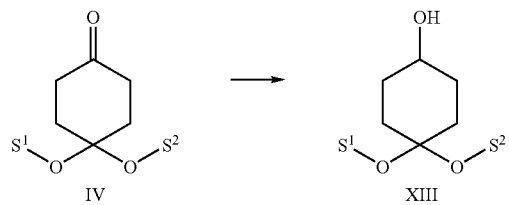

b. which is then reacted in the presence of an inorganic, organometallic or organic base with an alkyl or aryl bromide, chloride, iodide or triflate or with an alkane or aromatic compound $R^4X$ provided with a different leaving group X, to give a compound according to formula XIV;

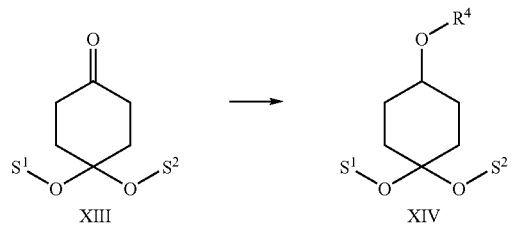

c. on the compound according to formula XIV, the protecting groups $S^1$ and $S^2$ are split off, so that a compound according to formula XV is formed;

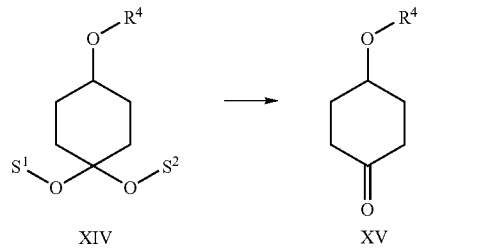

d. the compound of formula XV is reacted with cyanide, preferably potassium cyanide, in the presence of a compound of the formula $HNR^{O1}R^{O2}$ to give an α-aminonitrile derivative of formula XVI;

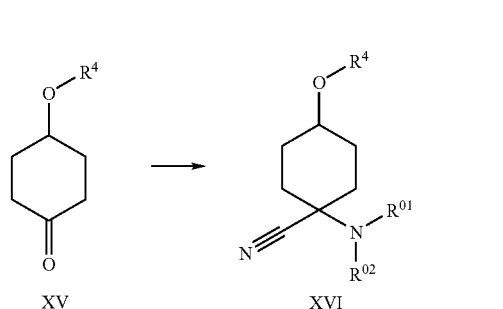

e. the α-aminonitrile derivative of formula XVI is reacted with organometallic reagents, preferably Grignard or organolithium reagents, of the formula metal-$R^3$ to give a compound according to formula I,
wherein $R^1$, $R^2$, $R^3$ and $R^4$ are as defined for compound group B and
$R^{O1}$ and $R^{O2}$ are selected independently of one another from H; H provided with a protecting group; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkylene, in each case mono- or poly-substituted or unsubstituted.

The invention further provides an alternative process for the preparation of the 4-aminocyclohexanols according to the invention of compound group C, comprising the following steps:

a. a cyclohexane-1,4-dione, protected with groups $S^1$ and $S^2$, according to formula IV is reacted with a reducing agent such as, for example, sodium borohydride, sodium cyanoborohydride, sodium triacetoxyborohydride, lithium aluminium hydride, diisobutylaluminium hydride, a complex analogue of these compounds, at temperatures of from −70° C. to +110° C., or with noble metal catalysis with hydrogen, to give a protected 4-hydroxycyclohexanone derivative according to formula XII;

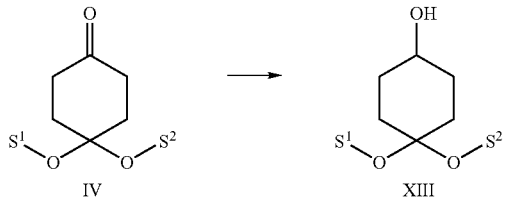

b. which is then reacted in the presence of an inorganic, organometallic or organic base with an alkyl-methyl, acyl-methyl or aryl-methyl bromide, chloride, iodide or triflate or with a methyl-alkane, methylcarboxylic acid or methyl aromatic compound $R^{11}$—$CH_2$—X provided with a different leaving group X, to give a compound according to formula XVII;

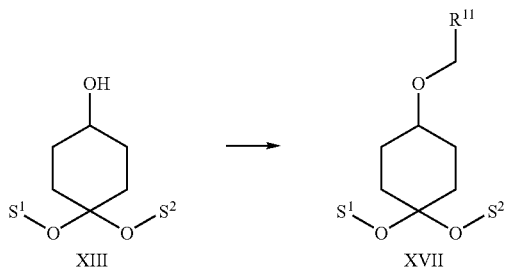

c. on the compound according to formula XVII, the protecting groups $S^1$ and $S^2$ are split off, so that a compound according to formula XVIII is formed;

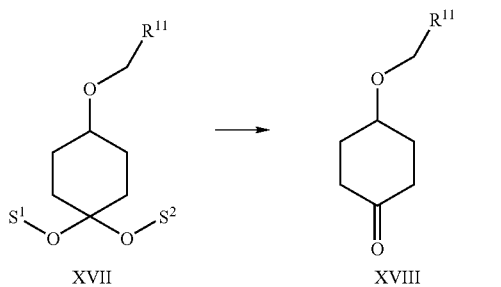

d. the compound of formula XVIII is reacted with cyanide, preferably potassium cyanide, in the presence of a compound of the formula $HNR^{O1}R^{O2}$ to give an α-aminonitrile derivative of formula XIX;

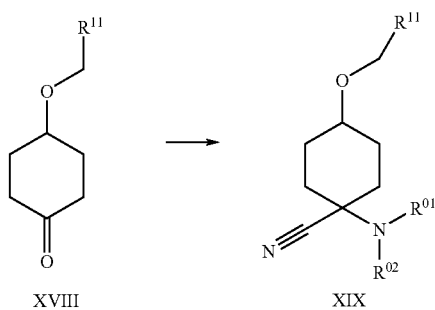

e. the α-aminonitrile derivative of formula XIX is reacted with organometallic reagents, preferably Grignard or organolithium reagents, of the formula metal-$R^3$ to give a compound according to formula II, wherein $R^1$, $R^2$, $R^3$ and $R^{11}$ are as defined for compound group C and $R^{O1}$ and $R^{O2}$ are selected independently of one another from H; H provided with a protecting group; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkylene, in each case mono- or poly-substituted or unsubstituted;

or the radicals $R^{O1}$ and $R^{O2}$ together form a ring and denote $CH_2CH_2OCH_2CH_2$, $CH_2CH_2NR^{O6}CH_2CH_2$ or $(CH_2)_{3-6}$.

The invention further provides an alternative process for the preparation of the 4-aminocyclohexanols according to the invention of compound group D, comprising the following steps:

a. a cyclohexane-1,4-dione, protected with groups $S^1$ and $S^2$, according to formula IV is reacted with a reducing agent such as, for example, sodium borohydride, sodium cyanoborohydride, sodium triacetoxyborohydride, lithium aluminium hydride, diisobutylaluminium hydride, a complex analogue of these compounds, at temperatures of from −70° C. to +110° C., or with noble metal catalysis with hydrogen, to give a protected 4-hydroxycyclohexanone derivative according to formula XIII;

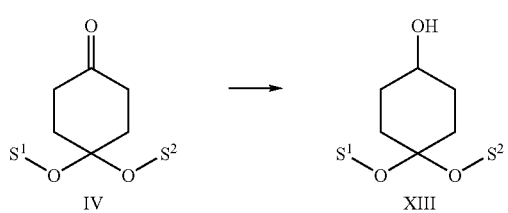

b. which is then reacted in the presence of an inorganic, organometallic or organic base with an alkyl, acyl or aryl bromide, chloride, iodide or triflate or with an alkane, carboxylic acid or aromatic compound $R^4X$ provided with a different leaving group X, to give a compound according to formula XIV;

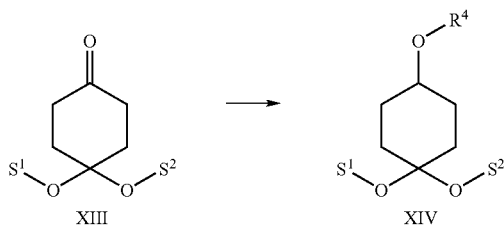

c. on the compound according to formula XIV, the protecting groups $S^1$ and $S^2$ are split off, so that a compound according to formula XV is formed;

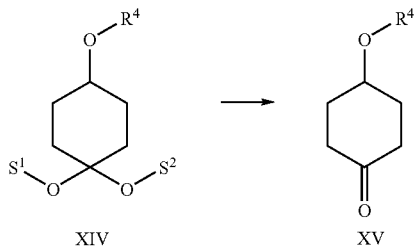

d. the compound of formula XV is reacted with cyanide, preferably potassium cyanide, in the presence of a compound of the formula $HNR^{O1}R^{O2}$ to give an α-aminonitrile derivative of formula XVI;

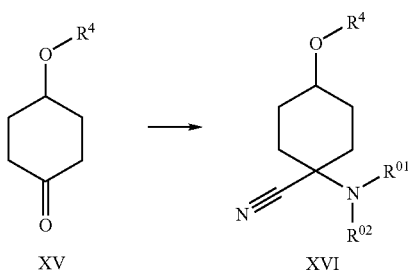

e. the aminonitrile derivative of formula XVI is reacted with organometallic reagents, preferably Grignard or organolithium reagents, of the formula metal-$CH_2$—$R^3$ to give a compound according to formula II,
wherein $R^1$, $R^2$, $R^{12}$ and $R^4$ are as defined for compound group D and
$R^{O1}$ and $R^{O2}$ are selected independently of one another from H; H provided with a protecting group; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkylene, in each case mono- or poly-substituted or unsubstituted;

or the radicals $R^{O1}$ and $R^{O2}$ together form a ring and denote $CH_2CH_2OCH_2CH_2$, $CH_2CH_2NR^{O6}CH_2CH_2$ or $(CH_2)_{3-6}$.

The invention is explained further hereinbelow by means of examples, without being limited thereto.

EXAMPLES

Certain embodiments of the present invention may be further understood by reference to the following specific examples. These examples and the terminology used herein are for the purpose of describing particular embodiments only and are not intended to be limiting.

The yields of the compounds prepared have not been optimized.

All temperatures are uncorrected.

The term "ether" means diethyl ether, "EE" means ethyl acetate and "DCM" means dichloromethane. The term "equivalents" means substance amount equivalents, "m.p." means melting point or melting range, "RT" means room temperature, "vol. %" means percent by volume, "wt. %" means percent by weight and "M" is the concentration stated in mol./l.

Silica gel 60 (0.040–0.063 mm) from E. Merck, Darmstadt, was employed as the stationary phase for the column chromatography.

The thin-layer chromatography analyses were carried out with HPTLC pre-coated plates, silica gel 60 F 254 from E. Merck, Darmstadt.

The mixing ratios of mobile phases for chromatography analyses are always stated in volume/volume.

Examples 1 & 2

(4-Benzyloxy-1-phenyl-cyclohexyl)dimethylamine hydrochloride, non-polar and polar diastereoisomer 350 g of 1,4-dioxa-spiro[4.5]decan-8-one were suspended in 2000 ml of ethanol, and 28.1 g of sodium borohydride were added in portions while cooling with an ice bath. After stirring overnight at room temperature, first 750 ml of phosphate buffer (pH 7, Merck-Darmstadt) and then 1000 ml of diethyl ether were added, with stirring, and precipitated solids were filtered and then washed with diethyl ether. The filtrate was dried over sodium sulfate, filtered and concentrated. 345 g of 1,4-dioxa-spiro[4.5]decan-8-ol were obtained in the form of a white solid.

225 g of 1,4-dioxa-spiro[4.5]decan-8-ol were dissolved in 1100 ml of dimethyl-formamide, and 198 g of potassium tert.-butoxide were added in portions, with stirring. After one hour, 223 g of benzyl chloride were added dropwise over 30 minutes, and stirred overnight. The batch was added to 1500 ml of water/ice mixture and extracted with ethyl acetate. The combined extracts were washed with saturated sodium chloride solution, dried over sodium sulfate, filtered and concentrated. The crude product was subjected to fractional distillation under a high vacuum. At 150° C. and a pressure of about 0.1 mbar, 294 g of 8-benzyloxy-1,4-dioxaspiro[4.5]decane were obtained.

294 g of 8-benzyloxy-1,4-dioxaspiro[4.5]decane were dissolved in 1400 ml of diisopropyl ether, and 580 ml of four molar hydrochloric acid were added. After 20 hours' stirring at room temperature, 300 ml of water and 180 ml of saturated sodium chloride solution were added, and stirring was carried out for a further four hours. The phases were separated, and the aqueous phase was neutralized with solid sodium hydrogen carbonate and extracted repeatedly with diisopropyl ether. The combined organic phases were dried over sodium sulfate, filtered and concentrated. Distillation under a high vacuum yielded 231 g of 4-benzyloxycyclohexanone.

A mixture of 130 ml of 7.9 molar aqueous dimethylamine solution, 16 ml of methanol, 20.0 g of 4-benzyloxycyclohexanone, 23.2 g of dimethylamine hydrochloride and 15.3 g of potassium cyanide was stirred for 65 hours at room temperature; extraction was carried out four times using 120 ml of diethyl ether each time, and the combined extracts were concentrated; 100 ml of dichloromethane were added to the residue, the phases were separated, and the organic phases were dried over sodium sulfate, filtered and concentrated. 24.5 g of 4-benzyloxy-1-dimethylaminocyclohexanecarbonitrile were obtained in the form of a yellowish oil which slowly solidified.

5.00 g of 4-benzyloxy-1-dimethylaminocyclohexanecarbonitrile were dissolved in 50 ml of tetrahydrofuran and, while cooling with an ice bath, 19.4 ml of two molar phenylmagnesium chloride solution in tetrahydrofuran were added dropwise under a nitrogen atmosphere. After stirring overnight at room temperature, cooling was again carried out in an ice bath, and 25 ml of cold ammonium chloride solution (20 percent by weight) were added. The phases were separated and extracted twice using 80 ml of diethyl ether each time, the combined organic phases were extracted three times using 60 ml of hydrochloric acid (5 percent by weight) each time, the combined acidic extracts were rendered weakly alkaline (pH 8–9) with aqueous ammonia solution (25 percent by weight), extraction was carried out three times using 80 ml of diethyl ether each time, and the combined organic extracts were dried over sodium sulfate, filtered and concentrated. The resulting yellow oil (4.15 g) was separated on silica gel with diethyl ether/hexane (V:V=1:1). 1.83 g of the non-polar and 0.38 g of the polar diastereoisomer of (4-benzyloxy-1-phenyl-cyclohexyl)dimethylamine were obtained in the form of a yellow solid and a yellow resin, respectively. 1.48 g of the non-polar diastereoisomer were dissolved in 11.8 ml of 2-butanone; 47 μl of water and 665 μl of chlorotrimethylsilane were added, and stirred overnight. The precipitated hydrochloride was filtered off, washed with diethyl ether and dried under a high vacuum. 1.55 g of the hydrochloride of the non-polar diastereoisomer of (4-benzyloxy-1-phenyl-cyclohexyl)dimethylamine (Example 1) were obtained in the form of a white solid. In an analogous manner, 300 mg of the corresponding hydrochloride (Example 2) were obtained from 379 mg of the polar diastereoisomer.

Example 3

(1-Benzyl-4-benzyloxy-cyclohexyl)dimethylamine Hydrochloride 4.00 g of 4-benzyloxy-1-dimethylaminocyclohexanecarbonitrile were dissolved in 40 ml of tetrahydrofuran, and 10.8 ml of two molar benzylmagnesium chloride solution in tetrahydrofuran were added dropwise under a nitrogen atmosphere, while cooling with an ice bath. After stirring overnight at room temperature, the mixture was again cooled in an ice bath, and 20 ml of cold ammonium chloride solution (20 percent by weight) were added. The phases were separated and extracted twice using 60 ml of diethyl ether each time, the combined organic phases were extracted three times using 50 ml of hydrochloric acid (5 percent by weight) each time, the combined acidic extracts were rendered weakly alkaline (pH 8–9) with aqueous ammonia solution (25 percent by weight) and extracted three times using 60 ml of diethyl ether each time, and the combined organic extracts were dried over sodium sulfate, filtered and concentrated. The resulting yellow solid (3.85 g) was separated on silica gel with diethyl ether/hexane (V:V=1:1). 2.45 g of (1-benzyl-4-benzyloxycyclo-hexyl)dimethylamine were obtained in the form of a white solid which, as described for Example 1, was converted into 2.03 g of the corresponding hydrochloride (white solid) using chlorotrimethylsilane and water in 2-butanone.

Example 4

[4-(2-Fluoro-benzyloxy)-1-phenyl-cyclohexyl]dimethylamine 200 ml of methanol, 1680 ml of aqueous dimethylamine solution (40 percent by weight), 303 g of dimethylamine hydrochloride and 200 g of potassium cyanide were added to 200 g of 1,4-dioxa-spiro[4.5]decan-8-one, and stirring was carried out for about 65 hours. The resulting white suspension was extracted four times using 800 ml of ether each time, the combined extracts were concentrated, the residue was taken up in about 500 ml of dichloromethane and the phases were separated. The dichloromethane phase was dried over sodium sulfate, filtered and concentrated. 265 g of 8-dimethylamino-1,4-dioxa-spiro[4.5]decane-8-carbonitrile were obtained in the form of a white solid.

50.0 g of 8-dimethylamino-1,4-dioxa-spiro[4.5]decane-8-carbonitrile were dissolved in 400 ml of analytical grade tetrahydrofuran; 216 ml of a commercially available two molar solution of phenylmagnesium chloride in tetrahydrofuran were added dropwise under a nitrogen atmosphere, while cooling with an ice bath, and stirring was carried out overnight at room temperature. For working up, 200 ml of ice-cold ammonium chloride solution (20 wt. %) were added with stirring, while cooling with an ice bath, and after 30 minutes the phases were separated. The aqueous phase was extracted twice using 250 ml of ether each time, and the extracts were combined with the organic phase, washed with 200 ml of water followed by 200 ml of saturated sodium chloride solution, dried over sodium sulfate, filtered and concentrated. 60.0 g of dimethyl-(8-phenyl-1,4-dioxa-spiro[4.5]dec-8-yl)-amine were obtained.

165 ml of hydrochloric acid (32 wt. %) were diluted with 100 ml of water; 60.0 g of dimethyl-(8-phenyl-1,4-dioxa-spiro[4.5]dec-8-yl)-amine were added to this approximately six molar hydrochloric acid, and stirring was carried out for 24 hours. The reaction mixture was washed three times using 50 ml of diethyl ether each time, rendered alkaline (pH>10) with 100 ml of sodium hydroxide solution (32 wt. %) and extracted three times using 100 ml of dichloromethane each time. The extracts were combined, dried over sodium sulfate, filtered and concentrated. 36.1 g of 4-dimethylamino-4-phenylcyclohexanone were obtained.

3.35 g of 4-dimethylamino-4-phenylcyclohexanone were suspended in 25 ml of isopropanol; 620 mg of sodium boranate were added, while cooling with an ice bath, and stirring was carried out overnight at room temperature. 6.5 ml of phosphate buffer (pH 7, Merck-Darmstadt) were added dropwise and the mixture was concentrated. The residue was taken up in 10 ml of water and 20 ml of diethyl ether and rendered alkaline with potassium hydroxide. The phases were separated and extracted three times using 15 ml of diethyl ether each time. The combined organic phases were dried over sodium sulfate, filtered and concentrated. 2.75 g of 4-dimethylamino-4-phenylcyclohexanol were obtained.

2.75 g of 4-dimethylamino-4-phenylcyclohexanol were dissolved in 20 ml of dimethylformamide; 1.55 g of potassium tert.-butoxide were added and stirring was carried out for 45 minutes, before 2.0 g of 2-fluorobenzyl chloride were added dropwise in the course of 30 minutes. After stirring overnight, the mixture was added to 25 ml of ice-water and extracted repeatedly with ethyl acetate. The combined extracts were washed with saturated sodium chloride solution, dried over sodium sulfate, filtered and concentrated. The resulting crude product (3.41 g) was separated on silica gel with methanol/ethyl acetate (V:V=1:1). 580 mg of [4-(2-fluoro-benzyloxy)-1-phenylcyclohexyl]dimethylamine were obtained in the form of a white solid which, as described for Example 1, was converted into 370 mg of the corresponding hydrochloride using chlorotrimethylsilane and water in 2-butanone.

Example 5

[1-Benzyl-4-(3-fluoro-benzyloxy)-cyclohexyl]dimethylamine 50.0 g of 8-dimethylamino-1,4-dioxa-spiro[4.5]decane-8-carbonitrile were dissolved in 400 ml of analytical grade tetrahydrofuran; 214 ml of a commercially available two molar solution of benzylmagnesium chloride in tetrahydrofuran were added dropwise under a nitrogen atmosphere, while cooling with an ice bath, and stirring was carried out overnight at room temperature. For working up, 200 ml of ice-cold ammonium chloride solution (20 percent by weight) were added with stirring, while cooling with an ice bath, and after 30 minutes the phases were separated. The aqueous phase was extracted twice using 250 ml of ether each time, and the extracts were combined with the organic phase, washed with 200 ml of water followed by 200 ml of saturated sodium chloride solution, dried over sodium sulfate, filtered and concentrated. 78.4 g of crude product were obtained, which consisted predominantly of (8-benzyl-1,4-dioxa-spiro[4.5]dec-8-yl)-dimethyl-amine and was reacted further without additional working up.

200 ml of hydrochloric acid (32 wt. %) were diluted with 120 ml of water; 78.4 g of crude (8-benzyl-1,4-dioxa-spiro [4.5]dec-8-yl)-dimethyl-amine were added to this approximately six molar hydrochloric acid, and stirring was carried out for 24 hours. The reaction mixture was washed three times using 100 ml of diethyl ether each time, rendered alkaline (pH>10) with 100 ml of sodium hydroxide solution (32 wt. %) while cooling with an ice bath, and extracted three times using 100 ml of dichloromethane each time. The extracts were combined, dried over sodium sulfate, filtered and concentrated. 50.4 g of 4-benzyl-4-dimethylamino-cyclohexanone were obtained.

40.0 g of 4-benzyl-4-dimethylamino-cyclohexanone were suspended in 250 ml of isopropanol; 19.9 g of sodium boranate were added, while cooling with an ice bath, and stirring was carried out overnight at room temperature. 65 ml of phosphate buffer (pH 7, Merck-Darmstadt) were added dropwise and the mixture was concentrated. The residue was taken up in water and dichloromethane and rendered alkaline with potassium hydroxide. The phases were separated and extracted three times with dichloromethane. The combined organic phases were dried over sodium sulfate, filtered and concentrated. 37.7 g of 4-benzyl-4-dimethylaminocyclohexanol were obtained.

2.65 g of 4-benzyl-4-dimethylaminocyclohexanol were dissolved in 20 ml of dimethylformamide; 1.40 g of potassium tert.-butoxide were added and stirring was carried out for 45 minutes, before 2.0 g of 3-fluorobenzyl chloride were added dropwise in the course of 30 minutes. After stirring overnight, the mixture was added to 25 ml of ice-water and extracted repeatedly with ethyl acetate. The combined extracts were washed with saturated sodium chloride solution, dried over sodium sulfate, filtered and concentrated. The resulting crude product (3.69 g) was separated on silica gel with hexane/ethyl acetate (V:V=1:1). 1.96 g of [1-benzyl-4-(3-fluoro-benzyloxy)-cyclohexyl]dimethylamine were obtained and, as described for Example 1, were converted into 1.13 g of the corresponding hydrochloride using chlorotrimethylsilane and water in 2-butanone (white solid).

Example 6

[1-Benzyl-4-(2-fluorobenzyloxy)cyclohexyl]dimethylamine 2.00 g of 4-benzyl-4-dimethylaminocyclohexanol were dissolved in 20 ml of dimethylformamide; 1.06 g of potassium tert.-butoxide were added and stirring was carried out for 45 minutes, before 1.36 g of 3-fluorobenzyl chloride were added dropwise in the course of 30 minutes. After stirring overnight, the mixture was added to 25 ml of ice-water and extracted repeatedly with ethyl acetate. The combined extracts were washed with saturated sodium chloride solution, dried over sodium sulfate, filtered and concentrated. The resulting crude product (2.98 g) was separated on silica gel with hexane/ethyl acetate (V:V=1:1). 913 mg of [1-benzyl-4-(2-fluorobenzyloxy)cyclohexyl]dimethylamine were obtained and, as described for Example 1, were converted into 620 mg of the corresponding hydrochloride using chlorotrimethylsilane and water in 2-butanone (white solid).

Example 7

[1-Benzyl-4-(4-fluoro-benzyloxy)-cyclohexyl]dimethylamine 2.00 g of 4-benzyl-4-dimethylaminocyclohexanol were dissolved in 20 ml of dimethylformamide; 1.06 g of potassium tert.-butoxide were added and stirring was carried out for 45 minutes, before 1.36 g of 4-fluorobenzyl chloride were added dropwise in the course of 30 minutes. After stirring overnight, the mixture was added to 25 ml of ice-water and extracted repeatedly with ethyl acetate. The combined extracts were washed with saturated sodium chloride solution, dried over sodium sulfate, filtered and concentrated. The resulting crude product (2.78 g) was separated on silica gel with hexane/ethyl acetate (V:V=1:1). 1.58 g of [1-benzyl-4-(4-fluorobenzyloxy)cyclohexyl]dimethylamine were obtained and, as described for Example 1, were converted into 890 mg of the corresponding hydrochloride using chlorotrimethylsilane and water in 2-butanone (white solid).

Example 8

[4-(2-Fluorobenzyloxy)-1-phenylcyclohexyl]dimethylamine 2.00 g of 4-dimethylamino-4-phenylcyclohexanol were dissolved in 20 ml of dimethylformamide; 1.13 g of potassium tert.-butoxide were added and stirring was carried out for 45 minutes, before 1.45 g of 2-fluorobenzyl chloride were added dropwise in the course of 15 minutes. After stirring overnight, the mixture was added to 25 ml of ice-water and extracted repeatedly with ethyl acetate. The combined extracts were washed with saturated sodium chloride solution, dried over sodium sulfate, filtered and concentrated. The resulting crude product (2.61 g) was separated on silica gel with hexane/diethyl ether (V:V=1:1). 1.08 g of [4-(2-fluorobenzyloxy)-1-phenylcyclohexyl]dimethylamine were obtained and, as described for Example 1, were converted into 970 mg of the corresponding hydrochloride using chlorotrimethylsilane and water in 2-butanone.

Example 9

[4-(3-Fluorobenzyloxy)-1-phenylcyclohexyl]dimethylamine 2.00 g of 4-dimethylamino-4-phenylcyclohexanol were dissolved in 20 ml of dimethylformamide; 1.13 g of potassium tert.-butoxide were added and stirring was carried out for 45 minutes, before 1.45 g of 3-fluorobenzyl chloride were added dropwise in the course of 15 minutes. After stirring overnight, the mixture was added to 25 ml of ice-water and extracted repeatedly with ethyl acetate. The combined extracts were washed with saturated sodium chloride solution, dried over sodium sulfate, filtered and concentrated. The resulting crude product (2.71 g) was separated on silica gel with hexane/diethyl ether (V:V=1:1). 996 mg of [4-(3-fluorobenzyloxy)-1-phenylcyclohexyl]dimethylamine were obtained and, as described for Example 1, were converted into 720 mg of the corresponding hydrochloride with chlorotrimethylsilane and water in 2-butanone.

Example 10

[4-(4-Fluorobenzyloxy)-1-phenylcyclohexyl]dimethylamine 2.00 g of 4-dimethylamino-4-phenylcyclohexanol were dissolved in 20 ml of dimethylformamide; 1.13 g of potassium tert.-butoxide were added and stirring was carried out for 45 minutes, before 1.45 g of 3-fluorobenzyl chloride were added dropwise in the course of 15 minutes. After stirring overnight, the mixture was added to 25 ml of ice-water and extracted repeatedly with ethyl acetate. The combined extracts were washed with saturated sodium chloride solution, dried over sodium sulfate, filtered and concentrated. The resulting crude product (2.66 g) was separated on silica gel with hexane/diethyl ether (V:V=1:1). 1.02 g of [4-(4-fluorobenzyloxy)-1-phenylcyclohexyl]dimethylamine were obtained and, as described for Example 1, were converted into 1.05 g of the corresponding hydrochloride using chlorotrimethylsilane and water in 2-butanone.

Example 11

(4-Benzyloxy-1-thiophen-2-yl-cyclohexyl)dimethylamine, non-polar and polar diastereoisomer 4.67 g of 2-iodothiophene were dissolved in 20 ml of tetrahydrofuran, and 7.26 ml of two molar isopropylmagnesium chloride solution in tetrahydrofuran were added dropwise under a nitrogen atmosphere, while cooling with an ice bath. After one hour, 2.50 g of 4-benzyloxy-1-dimethylaminocyclohexanecarbonitrile were added dropwise, dissolved in 10 ml of tetrahydrofuran. After stirring overnight at room temperature, the mixture was again cooled in an ice bath and 25 ml of cold ammonium chloride solution (20 wt. %) were added. The phases were separated and extracted three times using 40 ml of diethyl ether each time, and the combined organic phases were dried over sodium sulfate, filtered and concentrated. The resulting crude product (3.82 g) was separated on silica gel with diethyl ether. 1.59 g of the non-polar and 260 mg of the polar diastereoisomer of (4-benzyloxy-1-thiophen-2-yl-cyclohexyl)dimethylamine were obtained and, as described for Example 1, were converted into 1.11 g (Example 11) and 210 mg (Example 12) of the corresponding hydrochlorides using chlorotrimethylsilane and water in 2-butanone.

Examples 13 & 14

(1H-Indol-3-yl)-acetic acid 4-dimethylamino-4-phenyl-cyclohexyl ester hydrochloride, non-polar and polar diastereoisomer 175 mg of (1H-indol-3-yl)-acetic acid and 219 mg of 4-dimethylamino-4-phenyl-cyclohexanol (mixture of diastereoisomers analogously to Example 4) were added, under argon and while cooling with ice, to a mixture of 5 ml of dry dichloromethane and 5 ml of dry THF with 206 mg of dicyclohexylcarbodiimide and 12 mg of 4-dimethylaminopyridine, and stirring was carried out overnight. The resulting solid was filtered and washed with a small amount of diethyl ether. The resulting filtrate was concentrated and the residue was stirred for five minutes with a mixture of 10 ml of each of two molar sodium hydrogen carbonate solution and ethyl acetate. The phases were separated, the aqueous phase was extracted three times using 10 ml of ethyl acetate each time, and the combined organic phases were washed with 10 ml of water, dried over sodium sulfate and concentrated. The residue obtained was a mixture of the two possible diastereoisomeric esters, which were separated by chromatography on silica gel with methanol. 60 mg of the non-polar and 108 mg of the polar diastereoisomer were obtained in the form of colourless oils which, as described for Example 1, were converted into 65 mg (Example 13) and 118 mg (Example 14) of the corresponding hydrochlorides using chlorotrimethylsilane and water in 2-butanone.

Measurement of ORL1 Binding

The 4-aminocyclohexanol derivatives of the general formula I were investigated in a receptor binding assay with $^3$H-nociceptin/orphanin FQ with membranes of recombinant CHO—ORL1 cells. This test system was conducted in accordance with the method described by Ardati et al. (Mol. Pharmacol., 51, 1997, p. 816–824). The concentration of $^3$H-nociceptin/orphanin FQ in these experiments was 0.5 nM. The binding assays were carried out with in each case 20 μg membrane protein per 200 μl batch in 50 mM Hepes, pH 7.4, 10 mM $MgCl_2$ and 1 mM EDTA. The binding to the ORL1 receptor was determined using in each case 1 mg of WGA-SPA beads (Amersham-Pharmacia, Freiburg), by incubation of the batch for one hour at room temperature and subsequent measurement in a Trilux scintillation counter (Wallac, Finland). The affinity is given as the $K_i$ value.

Of each of these compounds of Examples 1 to 5, the affinity for the ORL1 receptor was determined according to the stated molecular-pharmacological investigations. The corresponding $K_i$ values are given in Table 1.

Analgesia Test in the Tail Flick Test in the Mouse

The mice were each placed individually into a test cage and the base of the tail was exposed to the focused heat ray of an electric lamp (tail-flick type 50/08/1.bc, Labtec, Dr. Hess). The intensity of the lamp was adjusted so that the time from switching on of the lamp to the sudden twitching away of the tail (latency of pain) in untreated mice was from 3 to 5 seconds. Before administration of the solutions comprising the compound according to the invention or of the particular comparison solutions, the mice were pre-tested twice in the course of five minutes and the mean of those measurements was calculated as the pre-test mean.

The solutions of the compound of the general formula I according to the invention and the comparison solutions were then administered intravenously. Pain measurement was carried out in each case 10, 20, 40 and 60 minutes following the intravenous administration. The analgesic activity was determined as the increase in the latency of pain (% of the maximum possible antinociceptive effect) according to the following formula:

$$[(T_1-T_0)/(T_2-T_0)] \times 100$$

where time $T_0$ is the latency before administration, time $T_1$ is the latency after administration of the active ingredient combination and time $T_2$ is the maximum exposure time (12 seconds).

TABLE 1

| Example | $K_i$ (µM) ORL1 binding assay | Antinociceptive activity in the tail flick test as a percentage relative to the control group* |
|---|---|---|
| 1 | 0.09 | 74 (1) |
| 2 | 0.40 | |
| 3 | 0.10 | 96 (1) |
| 4 | 0.20 | 53 (1) |
| 5 | 0.10 | 92 (1) |
| 6 | 0.40 | 68 (1) |
| 7 | 0.20 | 79 (1) |
| 8 | 0.10 | 46 (1) |
| 9 | 0.03 | 98 (1) |
| 10 | 0.04 | 96 (1) |
| 11 | 0.009 | 100 (10) |
| 12 | 0.25 | |
| 13 | 0.003 | |
| 14 | 0.09 | |

*the dosage in mg/kg in the case of intravenous administration is given in parenthesis in each case.

Parenteral Solution of a Substituted 4-aminocyclohexanol Derivative According to the Invention 38 g of one of the substituted 4-aminocyclohexanol derivatives according to the invention, in this case according to Example 11, are dissolved at room temperature in 1 litre of water for injection purposes and then adjusted to isotonic conditions by addition of anhydrous glucose for injection purposes.

The invention claimed is:

1. A substituted 4-aminocyckohexanol compound corresponding to formula I

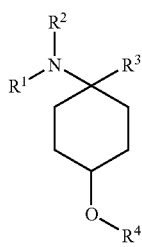

I wherein $R^1$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

$R^2$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

$R^3$ is selected from $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or $C_{3-8}$-cycloalkyl bonded via a $C_{1-3}$-alkyl bridge, in each case mono- or poly-substituted or unsubstituted; or heterocyclyl bonded via a $C_{1-3}$-alkyl bridge, saturated or unsaturated, mono- or poly-substituted or unsubstituted;

$R^4$ is selected from $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; or —$CHR^6R^7$, —$CHR^6$—$CH_2R^7$, —$CHR^6$—$CH_2$—$CH_2R^7$, —$CHR^6$—$CH_2$—$CH_2$—$CH_2R^7$ or —$R^8$-L-$R^9$, each of which may be bonded via a $C_1$-alkyl bridge where $R^6$ is selected from H; $C_{1-8}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; or $C(O)O$—$R^{10}$;

where $R^{10}$ is selected from $C_{1-7}$-alkyl, saturated or unsaturated, branched or unbranched, mono- or poly-substituted or unsubstituted; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted;

where $R^7$ is selected from

H; $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted, where $R^8$ is selected from $C_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted, where L is selected from —C(O)—NH—, —NH—C(O)—, —C(O)—O—, —O—C(O)—, —O—, —S— or —S(O)$_2$—, where R$^9$ is selected from H; C$_{1-8}$-alkyl, saturated or unsaturated, branched or unbranched, mono- or poly-substituted or unsubstituted; C$_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted, or a salt thereof with a physiologically tolerated acid, provided that when R$^1$ and R$^2$ represent H and R$^3$ represents CH$_3$, R$^4$ is not a group of the formula

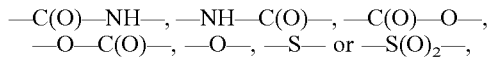

2. A substituted 4-aminocyclohexanol compound of claim 1, wherein said compound corresponds to formula II

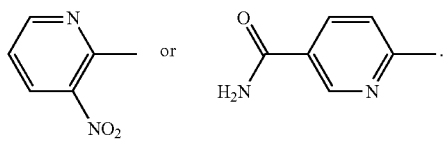

wherein

R$^{11}$ is selected from C$_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; —CHR$^6$R$^7$, —CHR$^6$—CH$_2$R$^7$, —CHR$^6$—CH$_2$—CH$_2$R$^7$; or —R$^8$-L-R$^9$.

3. A substituted 4-aminocyclohexanol compound of claim 1, wherein said compound corresponds to formula III

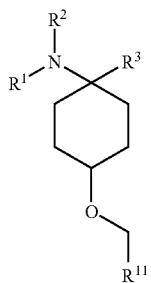

wherein

R$^{12}$ is selected from C$_{1-7}$-alkyl, saturated or unsaturated, branched or unbranched, mono- or poly-substituted or unsubstituted; C$_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or C$_{3-8}$-cycloalkyl bonded via a C$_{1-2}$-alkyl bridge, in each case mono- or poly-substituted or unsubstituted; or heterocyclyl bonded via a C$_{1-2}$-alkyl bridge, saturated or unsaturated, mono- or poly-substituted or unsubstituted.

4. A substituted 4-aminocyclohexanol compound according to claim 1, wherein

R$^1$ is selected from H or C$_{1-8}$-alkyl, saturated or unsaturated, branched or unbranched, mono- or poly-substituted or unsubstituted; and R$^2$ is selected from H or C$_{1-8}$-alkyl, saturated or unsaturated, branched or unbranched, mono- or poly-substituted or unsubstituted.

5. A substituted 4-aminocyclohexanol compound according to claim 1, wherein

R$^1$ is selected from H or C$_{1-4}$-alkyl, saturated or unsaturated, branched or unbranched, mono- or poly-substituted or unsubstituted; and R$^2$ is selected from H; C$_{1-4}$-alkyl, saturated or unsaturated, branched or unbranched, mono- or poly-substituted or unsubstituted; where R$^1$ and R$^2$ may not both be H.

6. A substituted 4-aminocyclohexanol compound according to claim 1, wherein R$^1$ and R$^2$ represent methyl.

7. A substituted 4-aminocyclohexanol compound according to claim 1 wherein

R$^3$ is selected from C$_{3-8}$-cycloalkyl, mono- or poly-substituted or unsubstituted; aryl, mono- or poly-substituted or unsubstituted; heterocyclyl, saturated or unsaturated, mono- or poly-substituted or unsubstituted; aryl or C$_{3-8}$-cycloalkyl bonded via a C$_{1-3}$-alkyl bridge, in each case mono- or poly-substituted or unsubstituted; or heterocyclyl bonded via a C$_{1-3}$-alkyl bridge, saturated or unsaturated, in each case mono- or poly-substituted or unsubstituted.

8. A substituted 4-aminocyclohexanol compound according to claim 1 wherein

R$^3$ is selected from C$_{5-6}$-cycloalkyl, unsubstituted or mono- or poly-substituted; phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, in each case unsubstituted or mono- or poly-substituted, or C$_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched C$_{1-2}$-alkyl group, in each case unsubstituted or mono- or poly-substituted.

9. A substituted 4-aminocyclohexanol compound according to claim 1 wherein

R$^3$ is selected from phenyl, pyridyl, furyl or thiophenyl, in each case unsubstituted or mono- or poly-substituted; or phenyl, pyridyl, furyl or thiophenyl bonded via a saturated, unbranched C$_{1-2}$-alkyl group, in each case unsubstituted or mono- or poly-substituted.

10. A substituted 4-aminocyclohexanol compound according to claim 1, wherein
R$^4$ is selected from C$_{3-8}$-cycloalkyl, aryl or heteroaryl, in each case unsubstituted or mono- or poly-substituted; or —R$^8$-L-R$^9$.

11. A substituted 4-aminocyclohexanol compound according to claim 1, wherein
R$^4$ is selected from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or poly-substituted; or —R$^8$-L-R$^9$.

12. A substituted 4-aminocyclohexanol compound according to claim 1, wherein
R$^4$ is selected from cyclopentyl, cyclohexyl, cycloheptyl, cyclooctyl, anthracenyl, indolyl, naphthyl, benzothiazolyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or poly-substituted; or —R$^8$-L-R$^9$.

13. A substituted 4-aminocyclohexanol compound according to claim 10, wherein at least one of R$^8$ and R$^9$ is selected from the group consisting of indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, pyrimidinyl, quinolinyl, isoquinolinyl, phthalazinyl and quinazolinyl, in each case unsubstituted or mono- or poly-substituted.

14. A substituted 4-aminocyclohexanol compound according to claim 1, wherein
R$^4$ is selected from —CHR$^6$R$^7$, —CHR$^6$—CH$_2$R$^7$, —CHR$^6$—CH$_2$—CH$_2$R$^7$, or —CHR$^6$—CH$_2$—CH$_2$—CH$_2$R$^7$.

15. A substituted 4-aminocyclohexanol compound according to claim 14, wherein
R$^6$ is selected from H, C$_{1-4}$-alkyl, saturated or unsaturated, branched or unbranched, mono- or poly-substituted or unsubstituted; or C(O)OR$^{10}$
where R$^{10}$ is selected from C$_{1-4}$-alkyl, saturated or unsaturated, branched or unbranched, mono- or poly-substituted or unsubstituted.

16. A substituted 4-aminocyclohexanol compound according to claim 14, wherein
R$^7$ is selected from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or poly-substituted.

17. The compound of claim 1, wherein said compound is present in the form of a free base.

18. The compound of claim 1, wherein said compound is present in the form of a pure enantiomer or pure diastereoisomer.

19. The compound of claim 1, wherein said compound is present in the form of a mixture of stereoisomers.

20. The compound of claim 1, wherein said compound is present in the form of a solvate.

21. The compound of claim 1, wherein said compound is present in the form of a hydrate.

22. A pharmaceutical formulation comprising: at least one substituted 4-aminocyclohexanol according to claim 1 with a suitable additive and optionally with further active ingredients.

23. A pharmaceutical formulation according to claim 22, wherein said pharmaceutical formulation further comprises an opioid.

24. A method of treating pain in a mammal, said method comprising administering to said mammal an effective pain alleviating amount of a compound according to claim 1.

25. A method for the treatment of anxiety, stress and syndromes associated with stress, depression, epilepsy, Alzheimer's disease, senile dementia, general cognitive dysfunctions, learning and memory difficulties (as a nootropic agent), withdrawal symptoms, alcohol or drug or substance abuse or dependency, sexual dysfunctions, cardiovascular diseases, hypotension, hypertension, tinnitus, pruritus, migraine, impaired hearing, deficient intestinal motility, impaired food intake, anorexia, obesity, locomotor disorders, diarrhea, cachexia, urinary incontinence or as a muscle relaxant, anticonvulsive or anaesthetic or for co-administration on treatment with an opioid analgesic or with an anaesthetic, for diuresis or antinatriuresis or anxiolysis in a mammal, said method comprising administering to said mammal a pharmaceutically effective amount of a compound according to claim 1.

26. A process for preparing a substituted 4-aminocyclohexanol compound according to claim 1, said process comprising the steps of:
a. reacting a cyclohexane-1,4-dione, protected with groups S$^1$ and S$^2$, corresponding to formula IV with a cyanide, in the presence of a compound corresponding to the formula HNR$^{01}$R$^{02}$ to give a protected N-substituted 1-amino-4-oxo-cyclohexanecarbonitrile derivative corresponding to formula V;

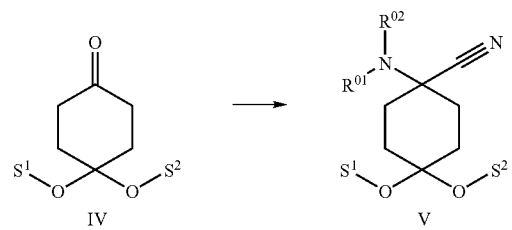

then optionally acylating, alkylating or sulfonating the resultant compound in any desired sequence and optionally repeatedly, or in the case of compounds where R$^{01}$ or R$^{02}$=H protected with a protecting group, a protecting group is split off at least once and acylation, alkylation or sulfonation is optionally carried out or in the case of compounds where R$^{01}$ or R$^{02}$=H, a protecting group is introduced at least once and acylation, alkylation or sulfonation is optionally carried out, b. reacting the aminonitrile according to formula V with organometallic reagents of the formula metal-$R^3$, so that a compound according to formula VI is formed;

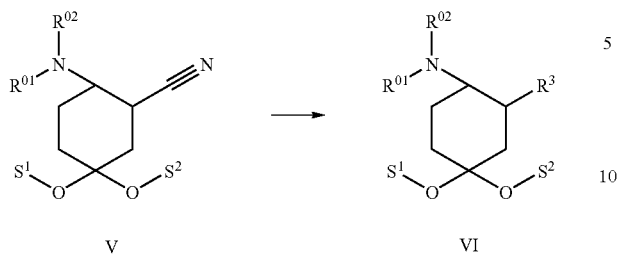

then optionally acylating, alkylating or sulfonating the resultant compound in any desired sequence and optionally repeatedly, or in the case of compounds where $R^{01}$ or $R^{02}$=H protected with a protecting group, splitting off a protecting group at least once and acylation, alkylation or sulfonation is optionally carried out or in the case of compounds where $R^{01}$ or $R^{02}$=H, introducing a protecting group at least once and acylation, alkylation or sulfonation is optionally carried out, c. splitting off the protecting groups $S^1$ and $S^2$ on the compound according to formula VI, so that a 4-substituted 4-aminocyclohexanone derivative according to formula VII is formed;

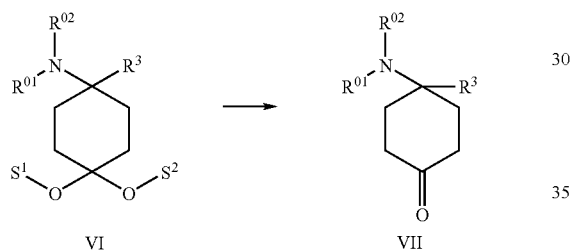

then optionally acylating, alkylating or sulfonating the resultant compound in any desired sequence and optionally repeatedly, or in the case of compounds where $R^{01}$ or $R^{02}$=H protected with a protecting group, a protecting group is split off at least once and acylation, alkylation or sulfonation is optionally carried out or in the case of compounds where $R^{01}$ or $R^{02}$=H, a protecting group is introduced at least once and acylation, alkylation or sulfonation is optionally carried out, d. reacting the 4-substituted 4-aminocyclohexanone derivative according to formula VII with a reducing agent at temperatures of from −70° C. to +110° C., or with noble metal catalysis with hydrogen, to give a 4-aminocyclohexanol derivative according to formula VIII;

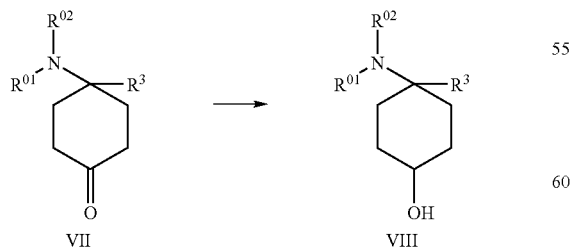

e. reacting the 4-substituted 4-aminocyclohexanol derivative according to formula VIII in the presence of an inorganic, organometallic or organic base with an alkyl, acyl or aryl bromide, chloride, iodide or triflate or with an alkane, alkyl acid or aromatic compound $R^4X$ provided with a different leaving group X to give a compound according to formula I, wherein $R^{01}$ and $R^{02}$ are selected independently of one another from H; H provided with a protecting group; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkylene, in each case mono- or poly-substituted or unsubstituted.

27. A process for the preparation of a substituted 4-aminocyclohexanol compound according to claim 2, said process comprising the steps of:

a. reacting a cyclohexane-1,4-dione, protected with groups $S^1$ and $S^2$, according to formula IV with a cyanide, in the presence of a compound of the formula $HNR^{01}R^{02}$ to give a protected N-substituted 1-amino-4-oxo-cyclohexanecarbonitrile derivative according to formula V;

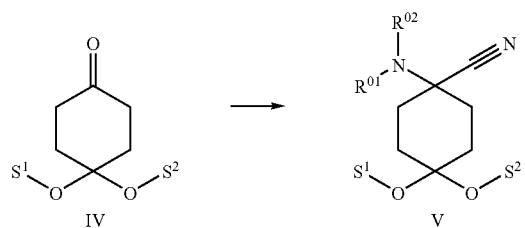

then optionally acylating, alkylating or sulfonating the resultant compound in any desired sequence and optionally repeatedly, or in the case of compounds where $R^{01}$ or $R^{02}$=H protected with a protecting group, a protecting group is split off at least once and acylation, alkylation or sulfonation is optionally carried out or in the case of compounds where $R^{01}$ or $R^{02}$=H, a protecting group is introduced at least once and acylation, alkylation or sulfonation is optionally carried out, b. reacting the aminonitrile according to formula V with organometallic reagents metal-$R^3$, so that a compound according to formula VI is formed;

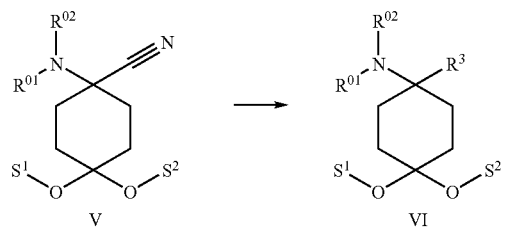

then optionally acylating, alkylating or sulfonating the resultant compound in any desired sequence and optionally repeatedly, or in the case of compounds where $R^{01}$ or $R^{02}$=H protected with a protecting group, a protecting group is split off at least once and acylation, alkylation or sulfonation is optionally carried out or in the case of compounds where $R^{01}$ or $R^{02}$=H, a protecting group is introduced at least once and acylation, alkylation or sulfonation is optionally carried out, c. splitting off the protecting groups $S^1$ and $S^2$ on the compound according to formula VI, so that a 4-substituted 4-aminocyclohexanone derivative according to formula VII is formed;

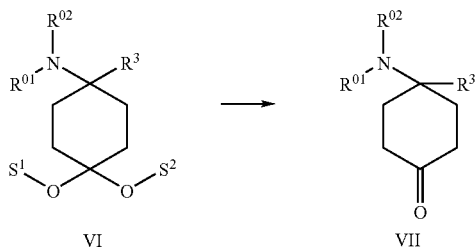

VI → VII then optionally acylating, alkylating or sulfonating the resultant compound in any desired sequence and optionally repeatedly, or in the case of compounds where $R^{01}$ or $R^{02}$=H protected with a protecting group, a protecting group is split off at least once and acylation, alkylation or sulfonation is optionally carried out or in the case of compounds where $R^{01}$ or $R^{02}$=H, a protecting group is introduced at least once and acylation, alkylation or sulfonation is optionally carried out, d. reacting the 4-substituted 4-aminocyclohexanone derivative according to formula VII with a reducing agent at temperatures of from −70° C. to +110° C., or with noble metal catalysis with hydrogen, to give a 4-aminocyclohexanol derivative according to formula VIII;

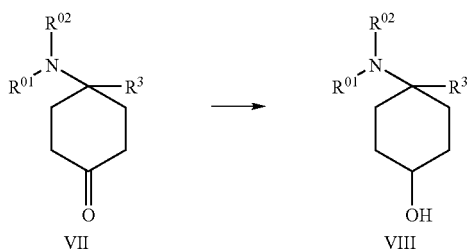

VII → VIII e. reacting the 4-substituted 4-aminocyclohexanol derivative according to formula VIII is in the presence of an inorganic, organometallic or organic base with an alkyl-methyl, acyl-methyl or aryl-methyl bromide, chloride, iodide or triflate or with an alkane-methyl, alkyl acid methyl or methyl aromatic compound of the formula $R^{11}$—$CH_2$—X provided with a different leaving group X to give a compound according to formula II, wherein $R^{01}$ and $R^{02}$ are selected independently of one another from H; H provided with a protecting group; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkylene, in each case mono- or poly-substituted or unsubstituted;

or the radicals $R^{01}$ and $R^{02}$ together form a ring and denote $CH_2CH_2OCH_2CH_2$, $CH_2CH_2NR^{06}CH_2CH_2$ or $(CH_2)_{3-6}$.

28. A process for the preparation of a substituted 4-aminocyclohexanol compound according to claim 3, said process comprising the steps of:

a. reacting a cyclohexane-1,4-dione, protected with groups $S^1$ and $S^2$, according to formula IV with a cyanide, in the presence of a compound of the formula $HNR^{01}R^{02}$ to give a protected N-substituted 1-amino-4-oxo-cyclohexanecarbonitrile derivative according to formula V;

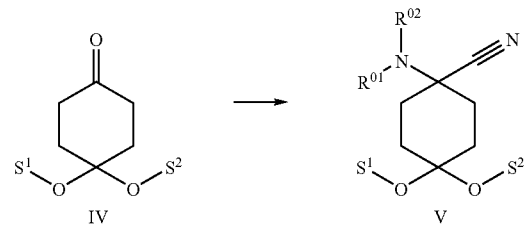

IV → V then optionally acylating, alkylating or sulfonating the resultant compound in any desired sequence and optionally repeatedly, or in the case of compounds where $R^{01}$ or $R^{02}$=H protected with a protecting group, a protecting group is split off at least once and acylation, alkylation or sulfonation is optionally carried out or in the case of compounds where $R^{01}$ or $R^{02}$=H, a protecting group is introduced at least once and acylation, alkylation or sulfonation is optionally carried out, b. reacting the aminonitrile according to formula V with organometallic reagents of the formula metal-$CH_2$—$R^{12}$, so that a compound according to formula IX is formed;

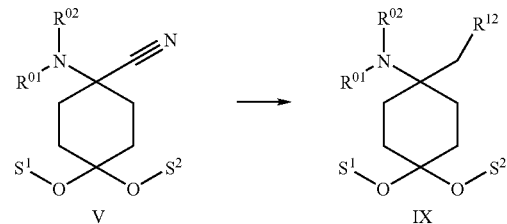

V → IX then optionally acylating, alkylating or sulfonating the resultant compound in any desired sequence and optionally repeatedly, or in the case of compounds where $R^{01}$ or $R^{02}$=H protected with a protecting group, a protecting group is split off at least once and acylation, alkylation or sulfonation is optionally carried out and/or in the case of compounds where $R^{01}$ or $R^{02}$=H, a protecting group is introduced at least once and acylation, alkylation or sulfonation is optionally carried out, c. splitting off the protecting groups $S^1$ and $S^2$ on the compound according to formula IX, so that a 4-substituted 4-aminocyclohexanone derivative according to formula XI is formed;

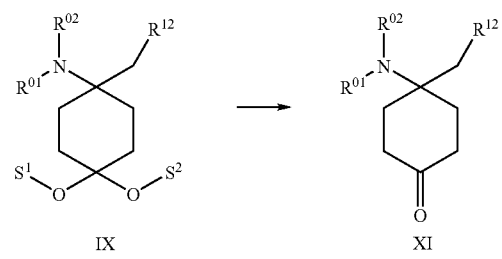

IX → XI then optionally acylating, alkylating or sulfonating the resultant compound in any desired sequence and optionally repeatedly, or in the case of compounds where $R^{O1}$ or $R^{O2}$=H protected with a protecting group, a protecting group is split off at least once and acylation, alkylation or sulfonation is optionally carried out or in the case of compounds where $R^{O1}$ or $R^{O2}$=H, a protecting group is introduced at least once and acylation, alkylation or sulfonation is optionally carried out, d. reacting the 4-substituted 4-aminocyclohexanone derivative according to formula XI with a reducing agent at temperatures of from −70° C. to +110° C., or with noble metal catalysis with hydrogen, to give a 4-aminocyclohexanol derivative according to formula XII;

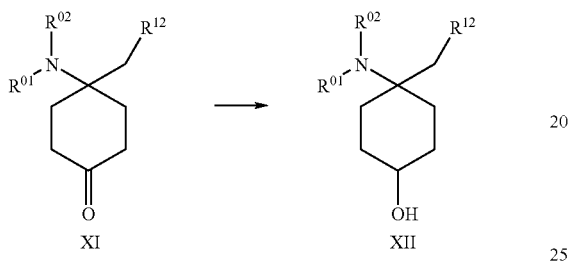

e. reacting the 4-substituted 4-aminocyclohexanol derivative according to formula XII in the presence of an inorganic, organometallic or organic base with an alkyl, acyl or aryl bromide, chloride, iodide or triflate or with an alkane, alkyl acid or aromatic compound $R^4X$ provided with a different leaving group X to give a compound according to formula III, wherein $R^{O1}$ and $R^{O2}$ are selected independently of one another from H; H provided with a protecting group; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkylene, in each case mono- or poly-substituted or unsubstituted;

or the radicals $R^{O1}$ and $R^{O2}$ together form a ring and denote $CH_2CH_2OCH_2CH_2$, $CH_2CH_2NR^{O6}CH_2CH_2$ or $(CH_2)_{3-6}$.

29. A process for the preparation of a substituted 4-aminocyclohexanol according to claim 1, said process comprising the steps of:

a. reacting a cyclohexane-1,4-dione, protected with groups $S^1$ and $S^2$, according to formula IV with a reducing agent at temperatures of from −70° C. to +110° C., or with noble metal catalysis with hydrogen, to give a protected 4-hydroxycyclohexanone derivative according to formula XIII;

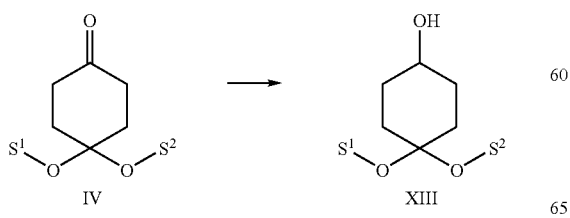

b. reacting the resultant compound in the presence of an inorganic, organometallic or organic base with an alkyl or aryl bromide, chloride, iodide or triflate or with an alkane or aromatic compound $R^4X$ provided with a different leaving group X, to give a compound according to formula XIV;

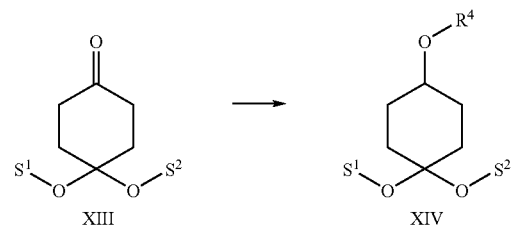

c. splitting off the protecting groups $S^1$ and $S^2$ on the compound according to formula XIV, so that a compound according to formula XV is formed;

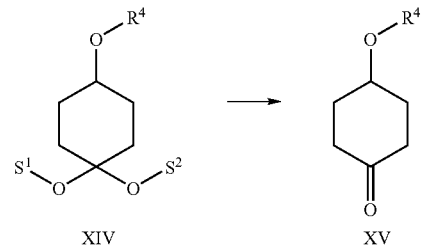

d. reacting the compound of formula XV with cyanide, in the presence of a compound of the formula $HNR^{O1}R^{O2}$ to give an α-aminonitrile derivative of formula XVI;

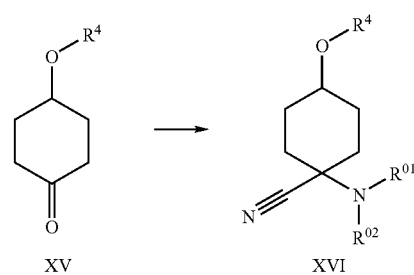

e. reacting the α-aminonitrile derivative of formula XVI with organometallic reagents, of the formula metal-$R^3$ to give a compound according to formula I, wherein $R^{O1}$ and $R^{O2}$ are selected independently of one another from H; H provided with a protecting group; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkylene, in each case mono- or poly-substituted or unsubstituted.

30. A process for the preparation of a substituted 4-aminocyclohexanol compound according to claim 2, comprising the steps of:

a. reacting a cyclohexane-1,4-dione, protected with groups $S^1$ and $S^2$, according to formula IV with a reducing agent at temperatures of from −70° C. to +110° C., or with noble metal catalysis with hydrogen, to give a protected 4-hydroxycyclohexanone derivative according to formula XIII;

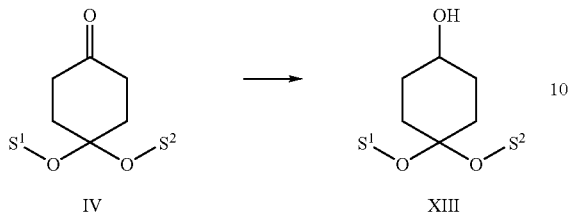

b. reacting the resultant compound in the presence of an inorganic, organometallic or organic base with an alkyl-methyl, acyl-methyl or aryl-methyl bromide, chloride, iodide or triflate or with a methyl-alkane, methylcarboxylic acid or methyl aromatic compound $R^{11}$—$CH_2$—X provided with a different leaving group X, to give a compound according to formula XVII;

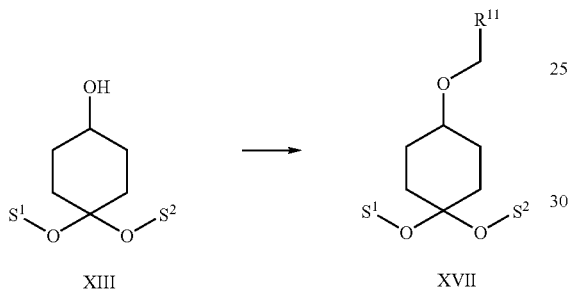

c. splitting off the protecting groups $S^1$ and $S_2$ on the compound according to formula XVII, so that a compound according to formula XVIII is formed;

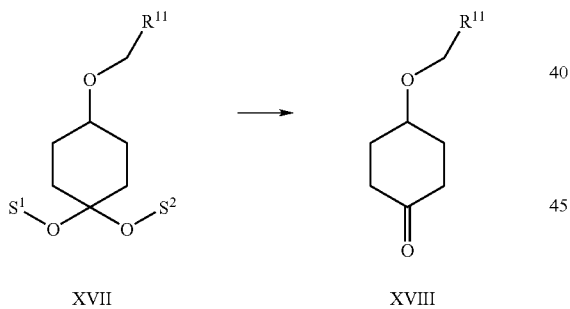

d. reacting the compound of formula XVIII with cyanide, in the presence of a compound of the formula $HNR^{o1}R^{o2}$ to give an α-aminonitrile derivative of formula XIX;

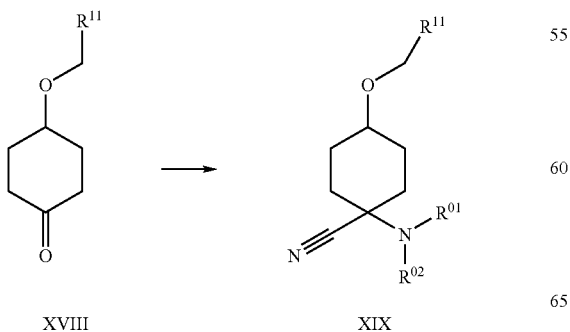

e. reacting the α-aminonitrile derivative of formula XIX with organometallic reagents, of the formula metal-$R^3$ to give a compound according to formula II, wherein $R^{o1}$ and $R^{o2}$ are selected independently of one another from H; H provided with a protecting group; $C_{1-8}$-alkyl or $C_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkylene, in each case mono- or poly-substituted or unsubstituted.

31. A process for the preparation of a substituted 4-aminocyclohexanol compound according to claim 4, comprising the steps of:

a. reacting a cyclohexane-1,4-dione, protected with groups $S^1$ and $S^2$, according to formula IV with a reducing agent at temperatures of from −70° C. to +110° C., or with noble metal catalysis with hydrogen, to give a protected 4-hydroxycyclohexanone derivative according to formula XIII;

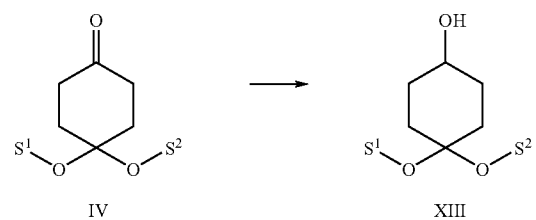

b. reacting the resultant compound in the presence of an inorganic, organometallic or organic base with an alkyl, acyl or aryl bromide, chloride, iodide or triflate or with an alkane, carboxylic acid or aromatic compound $R^4X$ provided with a different leaving group X, to give a compound according to formula XIV;

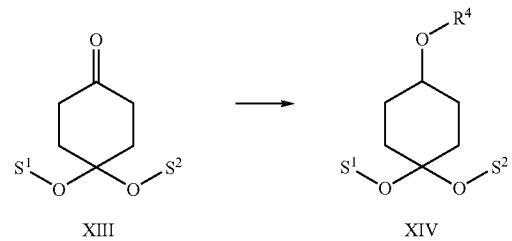

c. splitting off the protecting groups $S^1$ and $S^2$ on the compound according to formula XIV, so that a compound according to formula XV is formed;

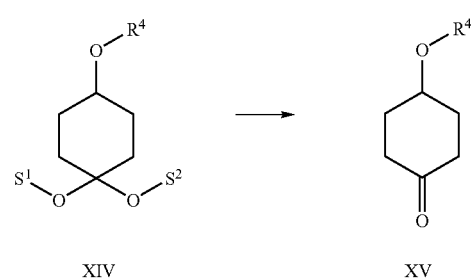

d. reacting the compound of formula XV with cyanide, in the presence of a compound of the formula HNR$^{O1}$R$^{O2}$ to give an α-aminonitrile derivative of formula XVI;

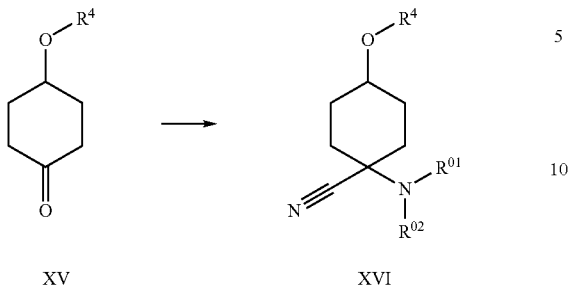

e. reacting the aminonitrile derivative of formula XVI with organometallic reagents, of the formula metal-CH$_2$—R$^3$ to give a compound according to formula III, wherein R$^{O1}$ and R$^{O2}$ are selected independently of one another from H; H provided with a protecting group; C$_{1-8}$-alkyl or C$_{3-8}$-cycloalkyl, in each case saturated or unsaturated, branched or unbranched, mono- or poly-substituted or unsubstituted; aryl or heteroaryl, in each case mono- or poly-substituted or unsubstituted; or aryl, C$_{3-8}$-cycloalkyl or heteroaryl bonded via C$_{1-3}$-alkylene, in each case mono- or poly-substituted or unsubstituted.

* * * * *